(12) United States Patent
Katayama et al.

(10) Patent No.: US 7,851,174 B2
(45) Date of Patent: Dec. 14, 2010

(54) METHOD FOR QUANTITATIVELY DETERMINING CHOLESTEROL IN HIGH DENSITY LIPOPROTEINS AND REAGENTS THEREFOR

(75) Inventors: Yuki Katayama, Mishima (JP); Mayumi Fujinaka, Mishima (JP)

(73) Assignee: Kyowa Medex Co., Ltd., Tokyo (JP)

(*) Notice: Subject to any disclaimer, the term of this patent is extended or adjusted under 35 U.S.C. 154(b) by 261 days.

(21) Appl. No.: 10/531,315

(22) PCT Filed: Oct. 16, 2003

(86) PCT No.: PCT/JP03/13258

§ 371 (c)(1),
(2), (4) Date: Apr. 13, 2005

(87) PCT Pub. No.: WO2004/035816

PCT Pub. Date: Apr. 29, 2004

(65) Prior Publication Data

US 2006/0014229 A1     Jan. 19, 2006

(30) Foreign Application Priority Data

Oct. 16, 2002   (JP)   .............. 2002-301327

(51) Int. Cl.
*C12Q 1/60* (2006.01)
*G01N 33/92* (2006.01)

(52) U.S. Cl. .............. 435/11; 435/19; 436/71

(58) Field of Classification Search .............. None
See application file for complete search history.

(56) References Cited

U.S. PATENT DOCUMENTS

| | | | |
|---|---|---|---|
| 4,521,519 A | 6/1985 | Draeger et al. | |
| 4,851,335 A | 7/1989 | Kerscher et al. | 435/11 |
| 4,892,815 A | 1/1990 | Kerscher et al. | 435/7 |
| 5,691,159 A | 11/1997 | Miyauchi et al. | |
| 5,736,406 A * | 4/1998 | Miyauchi et al. | 436/71 |
| 5,773,304 A | 6/1998 | Hino et al. | 436/174 |
| 5,888,755 A | 3/1999 | Miyauchi et al. | 435/11 |
| 6,162,607 A | 12/2000 | Miki et al. | |
| 6,479,249 B2 | 11/2002 | Matsui et al. | |
| 6,794,157 B1 | 9/2004 | Sugiuchi et al. | |
| 6,818,414 B1 | 11/2004 | Nakamura et al. | |
| 6,939,682 B2 | 9/2005 | Tamura et al. | |
| 7,208,287 B2 | 4/2007 | Kishi et al. | |
| 2002/0001819 A1 | 1/2002 | Matsui et al. | |
| 2004/0053350 A1 | 3/2004 | Yamamoto et al. | |
| 2004/0161811 A1 | 8/2004 | Kishi et al. | 435/11 |
| 2005/0250165 A1 | 11/2005 | Tamura et al. | |

FOREIGN PATENT DOCUMENTS

| | | |
|---|---|---|
| EP | 1 046 716 | 10/2000 |
| EP | 1 158 299 | 11/2001 |
| EP | 1 164 376 | 12/2001 |
| JP | 8-116996 | 5/1996 |
| JP | 9-285298 | 11/1997 |
| JP | 9285298 * | 11/1997 |
| WO | WO 95/24502 | 9/1995 |
| WO | WO 97/00971 | 1/1997 |
| WO | WO 97/40376 | 10/1997 |
| WO | WO97/40376 * | 10/1997 |
| WO | WO 00/52480 | 9/2000 |

OTHER PUBLICATIONS

U.S. Appl. No. 10/531,316, filed Apr. 13, 2005, Katayama, et al.

* cited by examiner

*Primary Examiner*—Lisa J Hobbs
(74) *Attorney, Agent, or Firm*—Fitzpatrick, Cella, Harper & Scinto

(57) ABSTRACT

A method for quantitatively determining cholesterol in high-density lipoprotein in a sample, which comprises: reacting a sample with i) cholesterol esterase and cholesterol oxidase or ii) cholesterol esterase, an oxidized coenzyme and cholesterol dehydrogenase in an aqueous medium comprising i) nonionic surfactant, polyanion and albumin or ii) a combination of a surfactant selected from the group consisting of polyoxyethylene alkylamine or polyoxyethylene alkenylamine and a surfactant selected from the group consisting of polyoxyethylene polycyclic phenyl ether sulfate and an anionic bile acid derivative, and measuring the formed hydrogen peroxide or a reduced coenzyme; and a reagent used therefor.

8 Claims, No Drawings

METHOD FOR QUANTITATIVELY DETERMINING CHOLESTEROL IN HIGH DENSITY LIPOPROTEINS AND REAGENTS THEREFOR

TECHNICAL FIELD

The present invention relates to a method for quantitatively determining cholesterol in high-density lipoprotein (hereinafter, abbreviated as HDL) in a sample, a reagent therefor and a kit therefor.

BACKGROUND ART

Depending upon their density, lipoproteins in living bodies are classified into high-density lipoprotein, low-density lipoprotein (hereinafter, abbreviated as LDL), very low-density lipoprotein (hereinafter, abbreviated as VLDL) and chylomicron (hereinafter, abbreviated as CM). Their functions in living body greatly differ mostly depending upon the difference in the kind of apoprotein and their lipid compositions vary as well. Among them, HDL relates to removal of cholesterol accumulated in cells by receiving cholesterol from various tissues including arterial wall and is a factor for the prevention of risk of various arteriosclerotic diseases such as coronary arteriosclerosis. HDL level in blood has been known to be useful for predicting the onset of arteriosclerotic diseases.

The conventional method for quantitatively determining cholesterol in HDL (hereinafter, abbreviated as HDL cholesterol) comprises two steps; a step of fractionation by an ultracentrifugal method, an immunochemical method, an electrophoretic method, a precipitation method, and the like; and a step of quantitative determination of cholesterol. However, the step of fractionation is complicated and takes a long time to operate, and moreover, there is a problem in terms of safely. Therefore, the measuring methods comprising such step of fractionation is not suitable for practical use because it is too inefficient.

In recent years, various measuring methods have been reported for solving the above problems. For example, there have been known, for example, a methods comprising mixing serum or plasma in a buffer comprising cholesterol esterase and cholesterol oxidase, and a salt of bile acid, a bile acid derivative or dioctyl sulfosuccinate, with the enzymes to react cholesterol in VLDL and LDL prior to HDL cholesterol, measuring the formed hydrogen peroxide, adding a nonionic surfactant having polyoxyethylene oxide group to the reaction solution to react HDL cholesterol with the enzymes and measuring HDL cholesterol fractionately (Japanese Published Unexamined Patent Application No. 69999/1987); and a measuring method for quantitatively determining HDL cholesterol comprising reacting serum, in a buffer comprising pancreas-derived cholesterol esterase, cholesterol oxidase, a bile acid-type surfactant and a nonionic surfactant, with the enzymes at a specific pH and specific temperature (Japanese Published Unexamined Patent Application No. 126498/1988). In a measuring method mentioned in the document 2, as the reaction of LDL cholesterol with the enzymes firstly proceeds and then reaction of HDL cholesterol with the enzymes proceeds, the determine HDL cholesterol can be done. However, those methods take a long time to operation and, moreover, they are not always specific to HDL cholesterol.

With regard to a method for quantitatively determining HDL cholesterol where lipoproteins other than HDL are aggregated, there have been known, for example, a measuring method using a reagent which aggregates lipoproteins other than HDL such as dextran sulfate, a divalent metal salt and a chemically modified enzyme (Japanese Published Unexamined Patent Application No. 131197/1996), a measuring method using a reagent which forms a complex with lipoproteins other than HDL such as polyanion and a surfactant which does not dissolve lipoprotein such as a polyoxyethylene-polyoxypropylene copolymer (Japanese Published Unexamined Patent Application No. 201393/1996), a measuring method using polyanion such as dextran sulfate, a divalent metal salt, a specific nonionic surfactant and albumin which is supplemented to the albumin contained in the sample (Japanese Published Unexamined Patent Application No. 285298/1997); a method for measuring HDL cholesterol in serum or plasma comprising treating serum or plasma with a solution comprising a lipoprotein fractionating agent (a combination of polyanion such as dextran sulfate with divalent cation such as magnesium ion), without separating the resulting mixture solution into solid and liquid, treating the solution with cholesterol esterase and cholesterol oxidase in the presence of anionic surfactant (alkyl sulfonate, bile acid or derivatives thereof), and measuring the formed hydrogen peroxide (Japanese Published Unexamined Patent Application No. 116996/1996), a method comprising adding a substance which forms a complex with lipoproteins other than HDL such as polyanion and a specific surfactant which does not dissolve lipoprotein to a biological specimen and measuring HDL cholesterol enzymatically (Japanese Published Unexamined Patent Application No. 201393/1996), and the like.

In those methods for quantitatively determining HDL cholesterol where lipoproteins other than HDL are aggregated, they have a good correlation to the conventional standard method. However, there are problems such as inaccuracy due to turbidity by aggregates formed in the reaction and an excessive load to autoanalyzer due to deposition of metal hydroxide produced in reaction cells by the reaction of metal salt in the reaction solution with an alkali used for washing of reaction cells.

With regard to a method for quantitatively determining HDL cholesterol without aggregation of lipoproteins other than HDL, there have been known, for example, a measuring method of HDL cholesterol comprising contacting a biological specimen with cholesterol esterase derived from pancreas and cholesterol oxidase in the presence of bile acid or a salt thereof and albumin, and measuring the compound which is consumed or produced by the enzymatic reaction of HDL cholesterol (International Publication WO 97/40376); a measuring method of HDL cholesterol in a sample comprising reacting a sample with cholesterol esterase and/or lipoprotein lipase acting on HDL fraction preferentially and cholesterol oxidase in the presence of a nonionic surfactant which has HLB value more than 16 as well as a reaction selectivity to the HDL fraction (International Publication WO 00/52840), and the like. In addition, a method where cholesterol in lipoproteins other than HDL is selectively converted to hydrogen peroxide using acylpolyoxyethylene sorbitan ester, the resulting hydrogen peroxide is eliminated and HDL cholesterol is enzymatically measured by adding polyoxyethylene alkyl ether (Japanese Published Unexamined Patent Application No. 299/1997) has been known as well.

However, in those methods for quantitatively determining HDL cholesterol where lipoproteins other than HDL are not aggregated, there may be a problem of inaccuracy of measured value caused by an incomplete elimination of cholesterol in lipoproteins other than HDL or by a non-specific reaction with cholesterol in lipoproteins other than HDL.

Further, when a specific substance in a sample is measured by an optical means, it has been a serious problem that turbidity caused by water-insoluble protein gives an optical effect to the determination in the case of sample which are derived from patients suffering from M proteinemia, myeloma and the like. In order to avid the optical effect, there has been commonly known a method that solves the turbidity caused by water-soluble protein by adjusting salt in the reaction solution at high concentration. However, in the quantitative determination of HDL cholesterol, there are some cases that presence of salt at high concentration may induce a decrease in specificity. Therefore, the quantitative determination of HDL cholesterol in the presence of a salt at high concentration is often very difficult.

DISCLOSURE OF THE INVENTION

An object of the present invention is to provide a simple and accurate method for quantitatively determining cholesterol in high-density lipoprotein in a sample and to provide a reagent and a kit used therefor.

The present invention relates to the following [1] to [37].

[1] A method for quantitatively determining cholesterol in high-density lipoprotein in a sample, which comprises:
  reacting a sample with i) cholesterol esterase and cholesterol oxidase or ii) cholesterol esterase, an oxidized coenzyme and cholesterol dehydrogenase in an aqueous medium comprising a nonionic surfactant, polyanion and albumin, and
  measuring the formed hydrogen peroxide or a reduced coenzyme.

[2] The method according to [1], wherein the aqueous medium further comprises a bile acid derivative.

[3] The method according to [2], wherein the bile acid derivative is an anionic bile acid derivative.

[4] The method according to any one of claims [1] to [3], wherein the nonionic surfactant is polyoxyethylene alkylamine or polyoxyethylene alkenylamine.

[5] The method according to any one of claims [1] to [4], wherein the polyanion is dextran sulfate or a salt thereof.

[6] A reagent for quantitatively determining cholesterol in high-density lipoprotein, which comprises a nonionic surfactant, polyanion, albumin, cholesterol esterase, cholesterol oxidase and a reagent for quantitatively determining hydrogen peroxide.

[7] A reagent for quantitatively determining cholesterol in high-density lipoprotein, which comprises a nonionic surfactant, polyanion, albumin, cholesterol esterase, cholesterol dehydrogenase and an oxidized coenzyme.

[8] The reagent according to [7], which further comprises a reagent for quantitatively determining a reduced coenzyme.

[9] The reagent according to any one of claims [6] to [8], which further comprises a bile acid derivative.

[10] The reagent according to [9], wherein the bile acid derivative is an anionic bile acid derivative.

[11] The reagent according to any one of [6] to [10], wherein the nonionic surfactant is polyoxyethylene alkylamine or polyoxyethylene alkenylamine.

[12] The reagent according to any one of [6] to [11], wherein the polyanion is dextran sulfate or a salt thereof.

[13] A kit for quantitatively determining cholesterol in high-density lipoprotein, which comprises a first reagent and a second reagent, wherein cholesterol esterase, polyanion, a nonionic surfactant, albumin and a reagent for quantitatively determining hydrogen peroxide are comprised in either or both of the first reagent and/or the second reagent, and cholesterol oxidase is comprised in the second reagent.

[14] A kit for quantitatively determining cholesterol in high-density lipoprotein, which comprises a first reagent comprising polyanion and a second reagent comprising cholesterol oxidase wherein cholesterol esterase, a nonionic surfactant, albumin and a reagent for quantitatively determining hydrogen peroxide are comprised in either or both of the first reagent and/or the second reagent.

[15] A kit for quantitatively determining cholesterol in high-density lipoprotein, which comprises a first reagent and a second reagent, wherein polyanion, a nonionic surfactant, albumin and an oxidized coenzyme are comprised in either or both of the first reagent and/or the second reagent, and cholesterol dehydrogenase is comprised in the second reagent.

[16] A kit for quantitatively determining cholesterol in high-density lipoprotein, which comprises a first reagent comprising polyanion and a second reagent comprising a cholesterol dehydrogenase, wherein cholesterol esterase, a nonionic surfactant, albumin and an oxidized coenzyme are comprised in either or both of the first reagent and/or the second reagent.

[17] The kit according to [15] or [16], which further comprises a reagent for quantitatively determining a reduced coenzyme in either or both of the first reagent and/or the second reagent.

[18] The kit according to any one of [13] to [17], which further comprises a bile acid derivative in either or both of the first reagent and/or the second reagent.

[19] The kit according to [18], wherein the bile acid derivative is an anionic bile acid derivative.

[20] The reagent according to any one of [13] to [19], wherein the nonionic surfactant is polyoxyethylene alkylamine or polyoxyethylene alkenylamine.

[21] The reagent according to any of [13] to [20], wherein the polyanion is dextran sulfate or a salt thereof.

[22] A method for quantitatively determining cholesterol in high-density lipoprotein in a sample, which comprises: reacting a sample with i) cholesterol esterase and cholesterol oxidase or ii) cholesterol esterase, an oxidized coenzyme and cholesterol dehydrogenase in an aqueous medium comprising i) a nonionic surfactant, polyanion and albumin or ii) a surfactant selected from the group consisting of polyoxyethylene alkylamine or polyoxyethylene alkenylamine and a surfactant selected from the group consisting of polyoxyethylene polycyclic phenyl ether sulfate and an anionic bile acid derivative, and measuring the formed hydrogen peroxide or a reduced coenzyme.

[23] A method for quantitatively determining cholesterol in high-density lipoprotein in a sample, which comprises reacting a sample with i) cholesterol esterase and cholesterol oxidase or ii) cholesterol esterase, an oxidized coenzyme and cholesterol dehydrogenase in an aqueous medium comprising a surfactant selected from the group consisting of polyoxyethylene alkylamine and polyoxyethylene alkenylamine and a surfactant selected from the group consisting of polyoxyethylene polycyclic phenyl ether sulfate and an anionic bile acid derivative, and measuring the formed hydrogen peroxide or a reduced coenzyme.

[24] The method according to [23], wherein the aqueous medium further comprises polyanion.

[25] The method according to [23] or [24], wherein the polyanion is dextran sulfate or a salt thereof.

[26] The method according to anyone of [23] to [25], wherein the aqueous medium further comprises albumin.

[27] A reagent for quantitatively determining cholesterol in high-density lipoprotein, which comprises polyoxyethylene alkylamine or polyoxyethylene alkenylamine, polyoxyethylene polycyclic phenyl ether sulfate or an anionic bile acid derivative, cholesterol esterase, cholesterol oxidase and a reagent for quantitatively determining hydrogen peroxide.

[28] A reagent for quantitatively determining cholesterol in high-density lipoprotein, which comprises polyoxyethylene alkylamine or polyoxyethylene alkenylamine, polyoxyethylene polycyclic phenyl ether sulfate or an anionic bile acid derivative, cholesterol esterase, cholesterol dehydrogenase and an oxidized coenzyme.

[29] The reagent according to [28], which further comprises a reagent for quantitatively determining a reduced coenzyme.

[30] The reagent according to any one of [17] to [29], which further comprises polyanion.

[31] The reagent according to [30], wherein the polyanion is dextran sulfate or a salt thereof.

[32] The reagent according to any of [17] to [31], which further comprises albumin.

[33] A kit for quantitatively determining cholesterol in high-density lipoprotein, which comprises a first reagent and a second reagent, wherein cholesterol esterase, polyoxyethylene alkylamine or polyoxyethylene alkenylamine, polyoxyethylene polycyclic phenyl ether sulfate or an anionic bile acid derivative and a reagent for quantitatively determining hydrogen peroxide are comprised in either or both of the first reagent and/or the second reagent, and cholesterol oxidase is comprised in the second reagent.

[34] A kit for quantitatively determining cholesterol in high-density lipoprotein, which comprises a first reagent and a second reagent, wherein cholesterol esterase, polyoxyethylene alkylamine or polyoxyethylene alkenylamine, polyoxyethylene polycyclic phenyl ether sulfate or an anionic bile acid derivative and an oxidized coenzyme are comprised in either or both of the first reagent and/or the second reagent, and cholesterol dehydrogenase is comprised in the second reagent.

[35] The kit according to [34], further comprising a reagent for quantitatively determining a reduced coenzyme in either or both of the first reagent and/or the second reagent.

[36] The kit according, to any one of [33] to [35], which further comprises polyanion in either or both of the first reagent and/or the second reagent.

[37] The kit according to any one of [33] to [37], which further comprises albumin in either or both of the first reagent and/or the second reagent.

The method for quantitatively determining HDL cholesterol according to the present invention is a method for quantitatively determining HDL cholesterol without eliminating cholesterol in lipoproteins other than HDL.

Examples of the sample used in the method according to the present invention are whole blood, plasma, serum, spinal fluid, saliva, amniotic fluid, urine, sweat, pancreatic fluid and the like and preferred ones are plasma and serum.

There is no particular limitation to the cholesterol esterase in the present invention so long as it is an enzyme having an ability to hydrolyze cholesterol ester, and it is possible to use, for example, cholesterol esterase and lipoprotein lipase derived from animals, plants and microorganisms as well as cholesterol esterase and lipoprotein lipase manufactured by means of genetic engineering.

With regard to the cholesterol esterase, both unmodified cholesterol esterase and chemically modified cholesterol esterase may be used. It is also possible to use cholesterol esterase which is available commercially.

Examples of the commercially available cholesterol esterase are cholesterol esterase "Amano" 2 (CHE2; manufactured by Amano Enzyme), cholesterol esterase "Amano" 3 (CHE3; manufactured by Amano Enzyme), lipoprotein lipase (LPL311; manufactured by Toyobo), lipoprotein lipase "Amano" 6 (LPL6; manufactured by Amano Enzyme), cholesterol esterase [COE313 (chemically modified cholesterol esterase); manufactured by Toyobo], and the like. It is also possible in the present invention to use two or more kinds of cholesterol esterases in combination.

Examples of the group which modifies the enzyme (chemically modifying group) in a chemical modification of cholesterol esterase include a group having poly(ethylene glycol) as a main component, a group having poly(propylene glycol) as a main component, a group having a copolymer of poly(propylene glycol) with poly(ethylene glycol), a group having a water-soluble polysaccharide, a sulfopropyl group, a sulfobutyl group, a polyurethane group, a group having a chelating function and the like. Among them, preferred one is a group having poly(ethylene glycol) as a main component. Examples of the water-soluble polysaccharide are dextran, pullulan, soluble starch and the like.

Examples of the reagent (chemical modifier agent) which chemically modifies the cholesterol esterase are compounds which have both the above chemically modifying group and a functional group or structure reactive with an amino group, a carboxyl group, a sulfhydryl group, etc. in the enzyme. Examples of the functional group or the structure reactive with an amino group in the enzyme are a carboxyl group, an activated ester group (such as an N-hydroxysuccinimide group), acid anhydride, acid chloride, aldehyde, an epoxide group, 1,3-propane sultone, 1,4-butane sultone and the like. Examples of the functional group or the structure reactive with a carboxyl group in the enzyme are an amino group, and the like. Examples of the group or the structure reactive with sulfhydryl group in the enzyme are a maleimide group, disulfide, α-haloester (such as α-iodoester) and the like.

With regard to a chemical modifier, commercially available modifier may be used. Examples of the commercially available chemical modifier are Sunbright VFM-4101, Sunbright MEAC-50HS and Sunbright MEC-50HS having both an N-hydroxylsuccinimide group and a group having poly (ethylene glycol) as a main component (all manufactured by NOF), Sunbright AKM series (such as Sunbright AKM-1510), Sunbright ADM series, Sunbright ACM series having both an acid anhydride structure and a group having poly (alkylene glycol) as a main component (all manufactured by NOF), EPOX-3400 and M-EPOX-5000 having both an epoxide group and a group having poly(ethylene glycol) as a main component (all manufactured by Sheawater Polymers) and diethylenetriamine-N,N,N',N'',N''-pentaacetic acid anhydride (DTPA anhydride) having both an acid anhydride structure and a group having a chelating function (manufactured by Dojindo Laboratories).

Chemical modification of cholesterol esterase may, for example, be carried out by the following method although there is no limitation thereto. Firstly, cholesterol esterase is dissolved in a buffer of pH 8.0 or higher (such as HEPES buffer) and chemical modifier is added in an amount of 0.01 to 500-fold molar quantity of the enzyme at 0 to 55° C. followed by stirring for 5 minutes to 5 hours. As chemically modified cholesterol esterase used in actual enzymatic reaction, not only the reaction solution as such but also a product where unreacted chemical modifier and the like are removed by, for example, ultrafiltration membrane if necessary may be used.

There is no particular limitation to the concentration of the cholesterol esterase used for the method of the present reaction so long as it enables the quantitative determination of HDL cholesterol of the present invention and, the concentration in the reaction solution is preferably, 0.01 to 200 U/mL and, more preferably, 0.02 to 100 U/mL.

There is no particular limitation to the cholesterol oxidase in the present invention so long as it is an enzyme having an ability to produce hydrogen peroxide by oxidizing cholesterol. For example, in addition to cholesterol-oxidase derived from animals, plants or microorganisms, it is possible to use cholesterol oxidase manufactured by means of genetic engineering. Commercially available ones such as cholesterol oxidase "Amano" 1 (CHOD1; manufactured by Amano Enzyme), cholesterol oxidase (CO-PE; manufactured by Kikkoman) and cholesterol oxidase (COO321; manufactured by Toyobo) may be used as well. In the present invention, two or more kinds of cholesterol oxidases may be used in combination.

The cholesterol oxidase may be either an unmodified enzyme or a chemically modified enzyme. Chemically modified cholesterol oxidase may, for example, be prepared by the above-mentioned chemically modifying method using the above-mentioned chemical modifier.

There is no particular limitation to the concentration of the cholesterol oxidase used for the method of the present reaction so long as it enables the quantitative determination of the HDL cholesterol of the present invention. It is preferred that a concentration in the reaction solution is 0.01 to 200 U/mL or, more preferably, 0.02 to 100 U/mL.

There is no particular limitation to the cholesterol dehydrogenase in the present invention so long as it is an enzyme having an ability to produce a reduced coenzyme by oxidation of cholesterol in the presence of an oxidized coenzyme. For example, in addition to cholesterol dehydrogenase derived from animals, plants and microorganisms, it is also possible to use cholesterol dehydrogenase manufactured by means of genetic engineering. Commercially available ones such as cholesterol dehydrogenase "Amano" 5 (CHDH5; manufactured by Amano) and the like may be used as well. In the present invention, two or more kinds of cholesterol dehydrogenases may be used in combination.

The cholesterol dehydrogenase may be either an unmodified enzyme or a chemically modified enzyme. Chemically modified cholesterol dehydrogenase may, for example, be prepared by the above-mentioned chemically modifying method using the above-mentioned chemical modifier.

There is no particular limitation to the concentration of the cholesterol dehydrogenase used for the method of the present reaction so long as it enables the quantitative determination of the HDL cholesterol of the present invention. It is preferred that a concentration in the reaction solution is 0.01 to 200 U/mL or, more preferably, 0.02 to 100 U/mL.

In a measuring method using the cholesterol dehydrogenase according to the present invention, an oxidized coenzyme is used. Examples of the oxidized coenzyme are NAD, NADP, thio-NAD, thio-NADP and the like.

There is no particular limitation to albumin used in the present invention so long as it is albumin that enables the quantitative determination of HDL cholesterol according to the present invention. Examples of the albumin are those derived from cattle, horse, sheep, human being and the like, and among them, bovine serum albumin (BSA) is preferred. It is also possible to use albumin manufactured by means of genetic engineering. In the present invention, two or more kinds of albumins having different origins may be used in combination. There is no particular limitation to the concentration of albumin in the quantitative determination of HDL cholesterol so long as it enables the quantitative determination of the HDL cholesterol of the present invention. It is preferred that a concentration in the reaction solution is 0.001 to 10% or, more preferably, 0.01 to 1%.

There is no particular limitation to the polyanion used in the present invention so long as it enables the quantitative of HDL cholesterol according to the present invention. Examples of the polyanion are dextran sulfate or a salt thereof, heparin or a salt thereof, phosphotungstic acid or a salt thereof, sulfated cyclodextrin or a salt thereof, sulfated oligosaccharide or a salt thereof, carageenan and the like, and among them, dextran sulfate or a salt thereof is preferred. Examples of dextran sulfate are dextran sulfate having molecular weight of 40,000, 80,000, 200,000, 500,000, 1,000,000, 2,000,000, and the like. Examples of the sulfated oligosaccharide are sulfated agarose, sulfated trehalose and chondroitin sulfate. Examples of the salt area sodium salt, a potassium salt, a lithium salt, an ammonium salt and a magnesium salt. In the present invention, two or more kinds of polyanion may be used in combination.

There is no particular limitation to the concentration of the polyanion used for the quantitative determination of HDL cholesterol so long as it enables the quantitative determination of the HDL cholesterol of the present invention. It is preferred that a concentration in the reaction solution is 0.001 to 10% or, more preferably, 0.01 to 1%.

There is no particular limitation to the nonionic surfactant used in the present invention so long as it enables the quantitative determination of HDL cholesterol of the present invention. Examples of the nonionic surfactant are polyoxyethylene alkylamine, polyoxyethylene alkenylamine, polyoxyethylene alkyl ether, polyoxyethylene alkenyl ether, polyoxyethylene aryl ether derivative, ethylenediamine tetrapolyoxyalkylene, and the like.

With regard to the nonionic surfactant, polyoxyethylene alkylamine and polyoxyethylene alkenylamine are preferred.

Examples of poloxyethylene alkylamine the polyoxyethylene alkenylamine are a compound represented by the formula (I) [hereinafter, referred to as Compound (I)]

(I)

[wherein R is a straight-chain or branched alkyl group or alkenyl group; X is a hydrogen atom or $(CH_2CH_2O)_nH$; m and n are the same or different, and each is an integer of 1 to 100; and m+n is an integer of 2 to 200.]

Examples of an alkyl group in the polyoxyethylene alkylamine, Compound (I) and polyoxyethylene alkyl ether include a straight-chain or branched alkyl having 6 to 30 carbon atoms such as hexyl, heptyl, octyl, isooctyl, nonyl, decyl, undecyl, dodecyl (lauryl), tridecyl, tetradecyl (myristyl, pentadecyl, hexadecyl (cetyl), heptadecyl, octadecyl (stearyl), nonadecyl, icosyl, henicosyl and docosyl (behenyl).

Examples of an alkenyl group in the polyoxyethylene alkenylamine, Compound (I) and polyoxyethylene alkenyl ether include a straight-chain or branched alkenyl having 6 to 30 carbon atoms such as hexenyl, heptenyl, octenyl, nonenyl, decenyl, citronellyl, undecenyl, dodecenyl, tridecenyl, tetradecenyl, pentadecenyl, hexadecenyl, heptadecenyl, oleyl, nonadecenyl, eicosenyl, henicosenyl, docosenyl, tricosenyl, tetracosenyl, pentacosenyl, hexacosenyl, heptacosenyl, octacosenyl, nonacosenyl and triacontenyl.

Specific examples (commercial products) of polyoxyethylene alkylamine or polyoxyethylene alkenylamine are Nymeen L201 (oxyethylene dodecylamine; manufactured by NOF), Nymeen L207 (polyoxyethylene dodecylamine; manufactured by NOF), Nymeen S204, Nymeen S210 (polyoxyethylene octadecylamine; manufactured by NOF), Newcol OD420 (polyoxyethylene octadecylamine; manufactured by Nippon Nyukazai), Pionin D3104 (polyoxyethylene laurylamine; manufactured by Takemoto Yushi), Pionin D3110 (polyoxyethylene laurylamine; manufactured by Takemoto Yushi), Pionin D3605 [polyoxyethylene alkyl(soybean) amine; manufactured by Takemoto Yushi], Pionin D3615T [polyoxyethylene alkyl (beef tallow) amine; manufactured by Takemoto Yushi], BLAUNON 209 (polyoxyethylene oleylamino ether; manufactured by Aoki Yushi), and the like.

Specific examples (commercial products) of polyoxyethylene alkyl ether or polyoxyethylene alkenyl ether are Emulmin L90S (polyoxyethylene lauryl ether; manufactured by Sanyo Chemical), Newcol 1310 (polyoxyethylene tridecyl ether; manufactured by Nippon Nyukazai), BLAUNON-EN 1520 (polyoxyethylene oleyl ether; manufactured by Aoki Yushi), and the like.

Examples of the polyoxyethylene aryl ether derivative are polyoxyethylene styrenated-phenyl ether, polyoxyalkylene styrenated-phenyl ether, polyoxyethylene styrenated-methylphenyl ether, polyoxyethylene styrenated-phenyl ether condensate, polyoxyethylene alkylphenyl ether, polyoxyethylene alkylphenyl ether formaldehyde condensate, and the like.

Specific examples (commercial products) of polyoxyethylene aryl ether derivative are Newcol 2604, Newcol 710 (both are polyoxyethylene polycyclic phenyl ether; manufactured by Nippon Nyukazai), Newcol 2608F (polyoxyalkylene polycyclic phenyl ether; manufactured by Nippon Nyukazai), Pionin D6310, Pionin D6320 (both are polyoxyethylene styrenated-phenyl ether condensate; manufactured by Takemoto Yushi), Nikkol R1020 (polyoxyethylene nonyl phenyl ether formaldehyde condensate; manufactured by Nikko Chemicals), and the like.

Examples of ethylenediamine tetrapolyoxyalkylene are ethylenediamine polyoxyethylene-polyoxypropylene condensate, ethylenediamine tetrapolyoxyethylene, ethylenediamine tetrapolyoxypropylene, and the like.

Specific examples (commercial products) of ethylenediamine tetrapolyoxyalkylene include Adeka Pullulonic TR704, Adeka Pullulonic TR701, AdekaPullulonic TR913R (all are ethylenediamine polyoxyethylene-polyoxypropylene condensates manufactured by Asahi Denka), Unilube 32TY-65BI (ethylenediamine tetrapolyoxyalkylene, manufactured by NOF), and the like.

The degree of polymerization of oxyalkylene chain (oxyethylene chain or oxypropylene chain) in polyoxyethylene alkylamine, polyoxyethylene alkenylamine, polyoxyethylene alkyl ether, polyoxyethylene alkenyl ether, a polyoxyethylene aryl ether derivative and ethylenediamine tetrapolyoxyalkylene is, preferably, 1 to 100, and, more preferably, 1 to 60.

Examples of polyoxyethylene polycyclic phenyl ether sulfate are polyoxyethylene styrenated-phenyl ether sulfate, polyoxyethylene benzylated-phenyl ether sulfate, and the like.

Specific examples (commercial products) of polyoxyethylene polycyclic phenyl ether sulfate are Newcol 707SF, 707SN, 714SF, 723SF, 740SF (all are manufactured by Nippon Nyukazai), and the like. The degree of polymerization of oxyethylene chain in polyoxyethylene polycyclic phenyl ether sulfate is, preferably, 1 to 100, and, more preferably, 5 to 40.

In the present invention, two or more nonionic surfactants may be used in combination. There is no particular limitation to a concentration of the nonionic surfactant in the method for quantitatively determining HDL cholesterol of the present invention so long as it enables the quantitative determination of HDL cholesterol according to the present invention. It is preferred that the concentration in the reaction solution is 0.0001 to 10% or, more preferably, 0.001 to 1%.

Examples of the bile acid derivative in the present invention are an anionic bile acid derivative, a amphoteric bile acid derivative, a nonionic bile acid derivative, and the like, and an anionic bile acid derivative is preferred.

Examples of the anionic bile acid derivative include cholic acid or a salt thereof, taurocholic acid or a salt thereof, glycocholic acid or a salt thereof, lithocholic acid or a salt thereof, deoxycholic acid or a salt thereof, chenodeoxycholic acid or a salt thereof, ursodeoxycholic acid or a salt thereof, 7-oxolithocholic acid or a salt thereof, 12-oxolithocholic acid or a salt thereof, 12-oxochenodeoxycholic acid or a salt thereof, 7-oxodeoxycholic acid or a salt thereof, hyocholic acid or a salt thereof, hyodeoxycholic acid or a salt thereof, dehydrocholic acid or a salt thereof, and the like. Examples of the salt are ammonium salt, lithium salt, sodium salt, potassium salt, magnesium salt, calcium salt, and the like.

Examples of the amphoteric bile acid derivative are a compound represented by the formula (II)

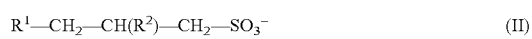

$$R^1-CH_2-CH(R^2)-CH_2-SO_3^- \qquad (II)$$

[wherein $R^1$ is a 3-(3-cholamidopropyl)dimethylammonio group and $R^2$ is a hydrogen atom or a hydroxyl group] [hereinafter, referred to as Compound (I)], and the like. Hereinafter, Compound (I) in which $R^2$ is a hydrogen atom will be referred to as CHAPS and Compound (I) in which $R^2$ is a hydroxyl group will be referred to as CHAPSO.

A example of the nonionic bile acid derivative is a compound represented by the formula (III)

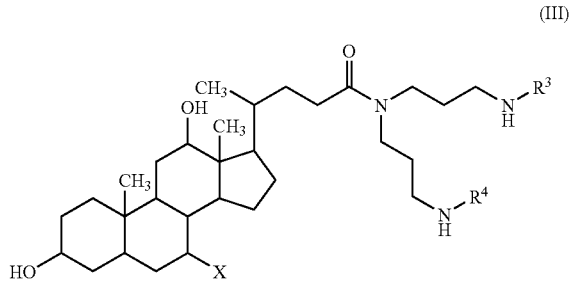

(wherein X is a hydrogen atom or a hydroxyl group; and $R^3$ and $R^4$ may be the same or different, and each represents a substituted or unsubstituted alkyl or a substituted or unsubstituted alkanoyl) [hereinafter, referred to as Compound (II)], and the like. Examples of alkyl moieties in the alkyl group and the alkanoyl group include a straight or branched alkyl having 1 to 10 carbon atoms such as methyl, ethyl, propyl, isopropyl, butyl, isobutyl, sec-butyl, tert-butyl, pentyl, neopentyl, hexyl, heptyl, octyl, nonyl, decyl, and the like. Examples of the substituent in the substituted alkyl group and the substituted alkanoyl group in Compound (III) are a hydroxyl group, a halogen atom, and the like. The halogen atom means each of fluorine, chlorine, bromine and iodine atoms. In the compound (III), a compound where both $R^3$ and $R^4$ are

$COCH(OH)CH(OH)CH(OH)CH(OH)CH_2OH$ (hereinafter, referred to as Substituent A) is preferred. Hereinafter, a compound in which X, $R^3$ and $R^4$ are a hydrogen atom, Substituent A and Substituent A, respectively, will be referred to as deoxy-BIGCHAP while a compound in which X, $R^3$ and $R^4$ are a hydroxyl group, Substituent A and Substituent A, respectively, will be referred to as BIGCHAP.

There is no particular limitation to a concentration of the bile acid derivative so long as it enables the quantitative determination of HDL cholesterol according to the present invention. Preferably, the concentration in the reaction solution is 0.001 to 10% and, more preferably, 0.01 to 1%.

Examples of an aqueous medium used in the method for the quantitative determination of HDL cholesterol according to the present invention are deionized water, distilled water, a buffer solution and the like. Among them, a buffer solution is preferred. Examples of a buffer used for the buffer solution are a tris(hydroxymethyl)aminomethane buffer, a phosphate buffer, a borate buffer, a Good's buffer and the like. Examples of a Good's buffer are 2-Morpholinoethanesulfonic acid (MES), bis-(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO), N-cyclohexyl-3-aminopropanesulfonic acid (CAPS), and the like. There is no particular limitation to the concentration of the buffer so long as it is a concentration suitable for the measurement and it is preferably, 0.001 to 2.0 mol/L and, more preferably, 0.005 to 1.0 mol/L.

Hereinafter, a method for the quantitative determination of HDL cholesterol, a reagent for the quantitative determination therefor and a kit for the quantitative determination therefor according to the present invention will be described in detail.

(Method for Quantitatively Determining HDL Cholesterol)

With regard to a method for quantitatively determining HDL cholesterol according to the present invention, methods of the following embodiments may be exemplified.

Method for the Measurement 1

HDL cholesterol in a sample can be quantitatively determined by (1) reacting a sample with i) cholesterol esterase and cholesterol oxidase or ii) cholesterol esterase, an oxidized coenzyme and cholesterol dehydrogenase in an aqueous medium comprising a nonionic surfactant, polyanion and albumin and, if necessary, further comprising a stabilizing agent, an antiseptic agent, an interfering substance elimination agent, a reaction promoter, and the like, (2) measuring the formed hydrogen peroxide or a reduced coenzyme in the presence, if necessary, of a reagent for quantitatively determining hydrogen peroxide or a reagent for quantitatively determining a reduced coenzyme, and (3) calculating an HDL cholesterol concentration in the sample by correlating the value obtained in (2) and a previously-prepared calibration curve.

Method for the Measurement 2

HDL cholesterol in a sample can be quantitatively determined by (1) reacting a sample with i) cholesterol esterase and cholesterol oxidase or ii) cholesterol esterase, an oxidized coenzyme and cholesterol dehydrogenase in an aqueous medium comprising a nonionic surfactant, polyanion, albumin and a bile acid derivative, and, if necessary, further comprising a stabilizing agent, an antiseptic agent, an interfering substance elimination agent, a reaction promoter, and the like, (2) measuring the formed hydrogen peroxide or a reduced coenzyme in the presence, if necessary, of a reagent for quantitatively determining hydrogen peroxide or a reagent for quantitatively determining a reduced coenzyme, and (3) calculating an HDL cholesterol concentration in the sample by correlating the value obtained in (2) and a previously-prepared calibration curve.

Method for the Measurement 3

HDL cholesterol in a sample can be quantitatively determined by (1) reacting a sample with i) cholesterol esterase and cholesterol oxidase or ii) cholesterol esterase, an oxidized coenzyme and cholesterol dehydrogenase in an aqueous medium comprising polyoxyethylene alkylamine or polyoxyethylene alkenylamine, and polyoxyethylene polycyclic phenyl ether sulfate or an anionic bile acid derivative, and, if necessary, further comprising polyanion, albumin, a stabilizing agent, an antiseptic agent, an interfering substance elimination agent, a reaction promoter, and the like, (2) measuring the formed hydrogen peroxide or a reduced coenzyme in the presence, if necessary, of a reagent for quantitatively determining hydrogen peroxide or a reagent for quantitatively determining a reduced coenzyme, and (3) calculating an HDL cholesterol concentration in the sample by correlating the value obtained in (2) and a previously-prepared calibration curve.

Method for the Measurement 4

HDL cholesterol in a sample can be quantitatively determined by 1) reacting a sample with i) cholesterol esterase and cholesterol oxidase or ii) cholesterol esterase, an oxidized coenzyme, and cholesterol dehydrogenase in an aqueous medium comprising polyoxyethylene alkylamine or polyoxyethylene alkenylamine, polyoxyethylene polycyclic phenyl ether sulfate or an anionic bile acid derivative, and an anionic bile acid derivative and, if necessary, further comprising polyanion, albumin, a stabilizing agent, an antiseptic agent, an interfering substance elimination agent, a reaction promoter, and the like, (2) measuring the formed hydrogen peroxide or a reduced coenzyme in the presence, if necessary, of a reagent for quantitatively determining hydrogen peroxide or a reagent for quantitatively determining a reduced coenzyme, and (3) calculating an HDL cholesterol concentration in the sample by correlating the value obtained in (2) and a previously-prepared calibration curve.

Examples of the aqueous medium are the above-mentioned aqueous medium, and the like. Examples of the stabilizing agent are ethylenediamine tetraacetic acid (EDTA), sucrose, calcium chloride, and the like. Examples of the antiseptic agent are sodium azide, antibiotic, and the like. Examples of the interfering substance elimination agent are ascorbate oxidase for elimination of interference by ascorbic acid, and the like. Examples of the reaction promoter are enzymes such as colipase and phospholipase, and salts such as sodium sulfate and sodium chloride.

In the present methods for the measurement, the reaction of (1) and (2) are carried out at, for example, 10 to 50° C. or, preferably, 20 to 40° C. for 1 to 60 minutes or, preferably, 2 to 30 minutes.

Amount of the produced hydrogen peroxide can be measured by, for example, a reagent for quantitatively determining hydrogen peroxide. A reagent for quantitatively determining hydrogen peroxide is a reagent for converting the formed hydrogen peroxide to a detectable substance. With regard to a detectable substance, dye, luminescence, and the like may be exemplified, and dye is preferred. When the detectable substance is a dye, the reagent for quantitatively determining hydrogen peroxide comprises an oxidative-coloring type of chromogen and a peroxidative substance such as peroxidase and the like. Examples of the oxidative-coloring type of chromogen are oxidative-coloring type of chromogens mentioned later. When the detectable substance is luminescence, a reagent for quantitatively determining hydrogen peroxide comprises a chemiluminescent substance. Examples of the chemiluminescent substance are luminol, isoluminol, lucigenin, acridinium ester and the like.

When a reagent comprising an oxidative-coloring type of chromogen and peroxidative substance such as peroxidase is used as a reagent for quantitatively determining hydrogen peroxide, hydrogen peroxide can be quantitatively determined by reacting the hydrogen peroxide with an oxidative-coloring type chromogen in the presence of peroxidative substance to form a dye, and measuring the formed dye. When a reagent for quantitatively determining hydrogen peroxide comprising a chemiluminescent substance is used, hydrogen peroxide can be quantitatively determined by reacting the hydrogen peroxide with a chemiluminescent substance to form photon and, measuring the formed photon.

Examples of the oxidative-coloring type of chromogen are a leuco type of chromogen and an oxidative coupling-coloring type of chromogen and the like. A leuco type of chromogen is a substance that is solely converted to a dye in the presence of hydrogen peroxide and a peroxidative substance such as peroxidase and the like.

Specific examples are 10-N-carboxymethylcarbamoyl-3,7-bis(dimethylamino)-10H-Phenothiazine (CCAP), 10-N-methylcarbamoyl-3,7-bis(dimethylamino)-10H-phenothiazine (MCDP), N-(carboxymethylaminocarbonyl)-4,4'-bis (dimethylamino)-diphenylamine sodium salt (DA-64), 4,4'-bis(dimethylamino)-diphenylamine, bis[3-bis(4-chlorophenyl)methyl-4-dimethylaminophenyl]amine (BCMA) and the like.

An oxidative coupling-coloring type of chromogen is a substance which gives a dye by an oxidized coupling of two compounds in the presence of hydrogen peroxide and a peroxidative substance such as peroxidase and the like. Examples of a combination of two compounds are a combination of a coupler with an aniline compound and a combination of a coupler with a phenol compound. Examples of the coupler are 4-aminoantipyrine 4-AA), 3-methyl-2-benzothiazolinone hydrazide and the like. Examples of the aniline compound are N-3-sulfopropyl)aniline, N-ethyl-N-2-hydroxyl-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl) aniline, N-ethyl-N-(3-methylphenyl)-N'-succinylethylenediamine (EMSE), N-ethyl-N-(3-methylphenyl)-N'-acetylethylenediamine, N-ethyl-N-(2-hydroxy-3-sulfopropyl)-4-fluoro-3,5-dimethoxyaniline (F-DAOS) and the like. Examples of the phenol compound are phenol, 4-chlorophenol, 3-methylphenol, 3-hydroxy-2,4,6-triiodobenzoic acid (HTIB) and the like.

In the quantitative determination of hydrogen peroxide, there is no particular limitation to the concentration of the peroxidative substance so long as it is suitable for the measurement and, when peroxidase is used as the peroxidative substance, it is preferably, 1 to 100 kU/L. Although there is no particular limitation to the concentration of an oxidative-coloring type of chromogen so long as it is a concentration which is suitable for the measurement and it is preferably 0.01 to 10 g/L.

Examples of a method for quantitatively determining a reduced coenzyme are a method where absorbance of the formed reduced coenzyme is determined and a method using a reagent for quantitatively determining a reduced coenzyme is used. With regard to a wavelength used in a method for the measurement of absorbance of a reduced coenzyme, 300 to 500 nm is preferred, 330 to 400 nm is more preferred and around 340 nm is particularly preferred. The reagent for quantitatively determining a reduced coenzyme is a reagent which converts the formed reduced coenzyme into a detectable substance. Examples of the detectable substance are a dye and the like. An example of the reagent for quantitatively determining a reduced coenzyme when the detectable substance is a dye, is a reagent comprising diaphorase, an electron carrier and reductive-coloring type of chromogen. Examples of the electron carrier are 1-methoxy-5-methylphenazium methyl sulfate, and the like. When a reagent comprising diaphorase, an electron carrier and a reductive-coloring type of chromogen is used as a reagent for quantitatively determining a reduced coenzyme, the reduced coenzyme can be quantitatively determined by measuring a dye which is given by conversion of the reductive-coloring type of chromogen.

Examples of the reductive-coloring type of chromogen are 3-(4,5-dimethyl-2-thiazolyl)-2,5-diphenyl-2H-tetrazolium bromide (MTT), 2-(4-iodophenyl)-3-(4-nitrophenyl)-5-(2,4-disulfophenyl)-2H-tetrazolium monosodium salt (WST-1), 2-(4-iodophenyl)-3-(2,4-dinitrophenyl)-5-(2,4-disulfophenyl)-2H-tetrazolium monosodium salt (WST-3) and the like.

(Reagent for Quantitatively Determining HDL Cholesterol)

Examples of the reagent for the quantitatively determining HDL cholesterol according to the present invention are the reagents of the following embodiments.

Reagent 1

A reagent comprising cholesterol esterase, cholesterol oxidase, a nonionic surfactant, polyanion, albumin and a reagent for quantitatively determining hydrogen peroxide.

Reagent 2

A reagent comprising cholesterol esterase, cholesterol oxidase, anonionic surfactant, polyanion, albumin, a bile acid derivative and a reagent for quantitatively determining hydrogen peroxide.

Reagent 3
A reagent comprising cholesterol esterase, cholesterol dehydrogenase, a nonionic surfactant, polyanion, albumin and an oxidized coenzyme.

Reagent 4
A reagent comprising cholesterol esterase, cholesterol dehydrogenase, a nonionic surfactant, polyanion, albumin, a bile acid derivative and an oxidized coenzyme.

Reagent 5
A reagent comprising cholesterol esterase, cholesterol dehydrogenase, a nonionic surfactant, polyanion, albumin, an oxidized coenzyme and a reagent for quantitatively determining a reduced coenzyme.

Reagent 6
A reagent comprising cholesterol esterase, cholesterol dehydrogenase, anonionicsurfactant, polyanion, albumin, a bile acid derivative, an oxidized coenzyme and a reagent for quantitatively determining a reduced coenzyme.

Reagent 7
A reagent comprising cholesterol esterase, cholesterol oxidase, polyoxyethylene alkylamine or polyoxyethylene alkenylamine, polyoxyethylene polycyclic phenyl ether sulfate and a reagent for quantitatively determining hydrogen peroxide.

Reagent 8
A reagent comprising cholesterol esterase, cholesterol oxidase, polyoxyethylene alkylamine or polyoxyethylene alkenylamine, an anionic bile acid derivative and a reagent for quantitatively determining hydrogen peroxide.

Reagent 9
A reagent comprising cholesterol esterase, cholesterol oxidase, polyoxyethylene alkylamine or polyoxyethylene alkenylamine, polyoxyethylene polycyclic phenyl ether sulfate, an anionic bile acid derivative and a reagent for quantitatively determining hydrogen peroxide.

Reagent 10
A reagent comprising cholesterol esterase, cholesterol dehydrogenase, polyoxyethylene alkylamine or polyoxyethylene alkenylamine, polyoxyethylene polycyclic phenyl ether sulfate and an oxidized coenzyme.

Reagent 11
A reagent comprising cholesterol esterase, cholesterol dehydrogenase, polyoxyethylene alkylamine or polyoxyethylene alkenylamine, an anionic bile acid derivative and an oxidized coenzyme.

Reagent 12
A reagent comprising cholesterol esterase, cholesterol dehydrogenase, polyoxyethylene alkylamine or polyoxyethylene alkenylamine, polyoxyethylene polycyclic phenyl ether sulfate, an anionic bile acid derivative and an oxidized coenzyme.

Reagent 13
A reagent comprising cholesterol esterase, cholesterol dehydrogenase, polyoxyethylene alkylamine or polyoxyethylene alkenylamine, polyoxyethylene polycyclic phenyl ether sulfate, an oxidized coenzyme and a reagent for quantitatively determining a reduced coenzyme.

Reagent 14
A reagent comprising cholesterol esterase, cholesterol dehydrogenase, polyoxyethylene alkylamine or polyoxyethylene alkenylamine, an anionic bile acid derivative, an oxidized coenzyme and a reagent for quantitatively determining a reduced coenzyme.

Reagent 15
A reagent comprising cholesterol esterase, cholesterol dehydrogenase, polyoxyethylene alkylamine or polyoxyethylene alkenylamine, polyoxyethylene polycyclic phenyl ether sulfate, an anionic bile acid derivative, an oxidized coenzyme and a reagent for quantitatively determining a reduced coenzyme.

In the reagent for quantitatively determining HDL cholesterol according to the present invention, cholesterol according to the present invention, such as cholesterol esterase, cholesterol oxidase, cholesterol dehydrogenase, a nonionic surfactant, polyanion, albumin, a bile acid derivative, a reagent for quantitatively determining hydrogen peroxide, an oxidized coenzyme and a reagent for quantitatively determining a reduced coenzyme which are mentioned in the above-mentioned method for the quantitative determination for HDL cholesterol according to the present invention may be used.

(Kit for Quantitatively Determining HDL Cholesterol)

The reagent for quantitatively determining HDL cholesterol according to the present invention may be preserved, circulated and used in a form of a kit. There is no particular limitation to a form of a kit. Examples of the form of a kit are a two-reagent system, a three-reagent system, and the like, and a two-reagent system is preferred.

In a kit for quantitatively determining HDL of a two-reagent system comprising a first reagent and a second reagent, cholesterol esterase and cholesterol oxidase or cholesterol dehydrogenase may be comprised in the first reagent and the second reagent separately or may be comprised together in the second reagent. In case they are comprised in the first reagent and the second reagent separately, a kit is preferred, where cholesterol esterase is comprised in the first reagent while cholesterol oxidase or cholesterol dehydrogenase is comprised in the second reagent. Polyanion may be comprised in either or both of the first reagent and/or the second reagent, and is, preferably, comprised in the first reagent. A nonionic surfactant and albumin may be comprised in either or both of the first reagent and/or the second reagent. An oxidized coenzyme used in a method for the measurement using cholesterol dehydrogenase may be comprised in either or both of the first reagent and/or the second reagent.

A reagent for quantitatively determining hydrogen peroxide may be comprised in either or both of the first reagent and/or the second reagent. When the reagent comprises an oxidative coupling-coloring type of chromogen, a kit is preferred, where each of the two components of oxidative coupling-coloring type of chromogen is comprised in the first or second reagent, separately. A reagent for quantitatively determining a reduced coenzyme may be comprised in either or both of the first reagent and/or the second reagent. A bile acid derivative may be comprised in either or both of the first reagent and/or the second reagent.

Examples of the kit of the present invention are the kits of the following embodiments.

A kit for quantitatively determining cholesterol in high-density lipoprotein, comprising the first reagent and the second reagent, wherein cholesterol esterase, polyanion, a nonionic surfactant, albumin and a reagent for quantitatively determining hydrogen peroxide are comprised in either or both of the first reagent and/or the second reagent, and cholesterol oxidase is comprised in the second reagent, and furthermore, if necessary, a bile acid derivative, a stabilizing agent, an antiseptic agent, an interfering substance elimination agent and a reaction promoter are comprised in either or both of the first reagent and/or the second reagent.

A kit for quantitatively determining cholesterol in high-density lipoprotein, comprising the first reagent and the second reagent, wherein polyanion is comprised in the first reagent and cholesterol oxidase is comprised in the second reagent, and cholesterol esterase, a nonionic surfactant, albumin and a reagent for quantitatively determining hydrogen peroxide are comprised in either or both of the first reagent and/or the second reagent, and furthermore, if necessary, a bile acid derivative, a stabilizing agent, an antiseptic agent, an interfering substance elimination agent and a reaction promoter are comprised in either or both of the first reagent and/or the second reagent.

A kit for quantitatively determining cholesterol in high-density lipoprotein, comprising the first reagent and the second reagent, wherein cholesterol esterase, polyanion, a nonionic surfactant, albumin and an oxidized coenzyme are comprised in either or both of the first reagent and/or the second reagent, and cholesterol dehydrogenase is comprised in the second reagent, and furthermore, if necessary, a bile acid derivative, a stabilizing agent, an antiseptic agent, an interfering substance elimination agent and a reaction promoter are comprised in either or both of the first reagent and/or the second reagent.

A kit for quantitatively determining cholesterol in high-density lipoprotein, comprising the first reagent and the second reagent, wherein polyanion is comprised in the first reagent and cholesterol dehydrogenase is comprised in the second reagent, and cholesterol esterase, a nonionic surfactant, albumin and an oxidized coenzyme are comprised in either or both of the first reagent and/or the second reagent, and furthermore, if necessary, a reagent for quantitatively determining a reduced coenzyme, a bile acid derivative, a stabilizing agent, an antiseptic agent, an interfering substance elimination agent and a reaction promoter are comprised in either or both of the first reagent and/or the second reagent.

A kit for quantitatively determining cholesterol in high-density lipoprotein, comprising the first reagent and the second reagent, wherein cholesterol esterase, polyoxyethylene alkylamine or polyoxyethylene alkenylamine, polyoxyethylene polycyclic phenyl ether sulfate or an anionic bile acid derivative and a reagent for quantitatively determining hydrogen peroxide are comprised in either or both of the first reagent and/or the second reagent, and cholesterol oxidase is comprised in the second reagent, and furthermore, if necessary, polyanion, albumin, a stabilizing agent, an antiseptic agent, an interfering substance elimination agent and a reaction promoter are comprised in either or both of the first reagent and/or the second reagent.

A kit for quantitatively determining cholesterol in high-density lipoprotein, comprising the first reagent and the second reagent, wherein cholesterol esterase, polyoxyethylene alkylamine or polyoxyethylene alkenylamine, polyoxyethylene polycyclic phenyl ether sulfate or an anionic bile acid derivative and an oxidized coenzyme are comprised in either or both of the first reagent and/or the second reagent, and cholesterol dehydrogenase is comprised in the second reagent, and furthermore, if necessary, a reagent for quantitatively determining a reduced coenzyme, polyanion, albumin, a stabilizing agent, an antiseptic agent, an interfering substance elimination agent and a reaction promoter are comprised in either or both of the first reagent and/or the second reagent.

To be more specific, the kits of the following embodiments will be exemplified. These Examples, of course, do not limit the scope of the present invention at all.

Kit 1

First Reagent

A reagent comprising cholesterol esterase, polyanion, albumin, a nonionic surfactant and a reagent for quantitatively determining hydrogen peroxide.

Second Reagent

A reagent comprising cholesterol oxidase and a reagent for quantitatively determining hydrogen peroxide.

Kit 2

First Reagent

A reagent comprising cholesterol esterase, polyanion, albumin, a nonionic surfactant, a bile acid derivative and a reagent for quantitatively determining hydrogen peroxide.

Second Reagent.

A reagent comprising cholesterol oxidase and a reagent for quantitatively determining hydrogen peroxide.

Kit 3

First Reagent

A reagent comprising cholesterol esterase, polyanion, albumin, a nonionic surfactant and a reagent for quantitatively determining hydrogen peroxide.

Second Reagent

A reagent comprising cholesterol oxidase, a bile acid derivative and a reagent for quantitatively determining hydrogen peroxide.

Kit 4

First Reagent

A reagent comprising polyanion, albumin, a nonionic surfactant and a reagent for quantitatively determining hydrogen peroxide.

Second Reagent

A reagent comprising cholesterol esterase, cholesterol oxidase and a reagent for quantitatively determining hydrogen peroxide.

Kit 5

First Reagent

A reagent comprising polyanion, albumin, a nonionic surfactant, a bile acid derivative and a reagent for quantitatively determining hydrogen peroxide.

Second Reagent

A reagent comprising cholesterol esterase, cholesterol oxidase and a reagent for quantitatively determining hydrogen peroxide.

Kit 6

First Reagent

A reagent comprising polyanion, albumin, a nonionic surfactant and a reagent for quantitatively determining hydrogen peroxide.

Second Reagent

A reagent comprising cholesterol esterase, cholesterol oxidase, a bile acid derivative and a reagent for quantitatively determining hydrogen peroxide.

Kit 7

First Reagent

A reagent comprising cholesterol esterase, polyanion, albumin and a nonionic surfactant.

Second Reagent

A reagent comprising cholesterol dehydrogenase and an oxidized coenzyme.

Kit 8

First Reagent

A reagent comprising cholesterol esterase, polyanion, albumin, a nonionic surfactant and a bile acid derivative Second Reagent.

A reagent comprising cholesterol dehydrogenase and an oxidized coenzyme.

Kit 9

First Reagent
A reagent comprising cholesterol esterase, polyanion, albumin and a nonionic surfactant.

Second Reagent
A reagent comprising cholesterol dehydrogenase, a bile acid derivative and an oxidized coenzyme.

Kit 10

First Reagent
A reagent comprising cholesterol esterase, polyanion, albumin and a nonionic surfactant.

Second Reagent
A reagent comprising cholesterol dehydrogenase, an oxidized coenzyme and a reagent for quantitatively determining a reduced coenzyme.

Kit 11

First Reagent
A reagent comprising cholesterol esterase, polyanion, albumin, a nonionic surfactant and a bile acid derivative Second Reagent.
A reagent comprising cholesterol dehydrogenase, an oxidized coenzyme and a reagent for quantitatively determining a reduced coenzyme.

Kit 12

First Reagent
A reagent comprising cholesterol esterase, polyanion, albumin and a nonionic surfactant.

Second Reagent
A reagent comprising cholesterol dehydrogenase, an oxidized coenzyme, a bile acid derivative and a reagent for quantitatively determining a reduced coenzyme.

Kit 13

First Reagent
A reagent comprising polyanion, albumin and a nonionic surfactant.

Second Reagent
A reagent comprising cholesterol esterase, cholesterol dehydrogenase and an oxidized coenzyme.

Kit 14

First Reagent
A reagent comprising polyanion, albumin and a nonionic surfactant.

Second Reagent
A reagent comprising cholesterol esterase, cholesterol dehydrogenase, an oxidized coenzyme and a bile acid derivative.

Kit 15

First Reagent
A reagent comprising polyanion, albumin, a nonionic surfactant and a bile acid derivative.

Second Reagent
A reagent comprising cholesterol esterase, cholesterol dehydrogenase and an oxidized coenzyme.

Kit 16

First Reagent
A reagent comprising polyanion, albumin and a nonionic surfactant.

Second Reagent
A reagent comprising cholesterol esterase, cholesterol dehydrogenase, an oxidized coenzyme and a reagent for quantitatively determining a reduced coenzyme.

Kit 17

First Reagent
A reagent comprising polyanion, albumin and a nonionic surfactant.

Second Reagent
A reagent comprising cholesterol esterase, cholesterol dehydrogenase, an oxidized coenzyme, a reagent for quantitatively determining a reduced coenzyme and a bile acid derivative.

Kit 18

First Reagent
A reagent comprising polyanion, albumin, a nonionic surfactant and a bile acid derivative.

Second Reagent
A reagent comprising cholesterol esterase, cholesterol dehydrogenase, an oxidized coenzyme and a reagent for quantitatively determining a reduced coenzyme.

Kit 19

First Reagent
A reagent comprising polyanion, albumin and a reagent for quantitatively determining hydrogen peroxide.

Second Reagent
A reagent comprising cholesterol esterase, cholesterol oxidase, a nonionic surfactant and a reagent for quantitatively determining hydrogen peroxide.

Kit 20

First Reagent
A reagent comprising polyanion, albumin, a bile acid derivative and a reagent for quantitatively determining hydrogen peroxide.

Second Reagent
A reagent comprising cholesterol esterase, cholesterol oxidase, a nonionic surfactant and a reagent for quantitatively determining hydrogen peroxide.

Kit 21

First Reagent
A reagent comprising polyanion, albumin and a reagent for quantitatively determining hydrogen peroxide.

Second Reagent
A reagent comprising cholesterol esterase, cholesterol oxidase, a nonionic surfactant, a bile acid derivative and a reagent for quantitatively determining hydrogen peroxide.

Kit 22

First Reagent
A reagent comprising polyanion and a reagent for quantitatively determining hydrogen peroxide.

Second Reagent
A reagent comprising cholesterol esterase, cholesterol oxidase, albumin, a nonionic surfactant and a reagent for quantitatively determining hydrogen peroxide.

Kit 23

First Reagent
A reagent comprising polyanion, a bile acid derivative and a reagent for quantitatively determining hydrogen peroxide.

Second Reagent

A reagent comprising cholesterol esterase, cholesterol oxidase, albumin, a nonionic surfactant and a reagent for quantitatively determining hydrogen peroxide.

Kit 24

First Reagent

A reagent comprising polyanion and a reagent for quantitatively determining hydrogen peroxide.

Second Reagent

A reagent comprising cholesterol esterase, cholesterol oxidase, albumin, a nonionic surfactant, a bile acid derivative and a reagent for quantitatively determining hydrogen peroxide.

Kit 25

First Reagent

A reagent comprising an anionic bile acid derivative and a reagent for quantitatively determining hydrogen peroxide Second Reagent A reagent comprising cholesterol esterase, cholesterol oxidase, polyoxyethylene alkylamine or polyoxyethylene alkenylamine and a reagent for quantitatively determining hydrogen peroxide.

Kit 26

First Reagent

A reagent comprising a reagent for quantitatively determining hydrogen peroxide.

Second Reagent

A reagent comprising cholesterol esterase, cholesterol oxidase, an anionic bile acid derivative, polyoxyethylene alkylamine or polyoxyethylene alkenylamine, and a reagent for quantitatively determining hydrogen peroxide.

Kit 27

First Reagent

A reagent comprising polyoxyethylene polycyclic phenyl ether sulfate and a reagent for quantitatively determining hydrogen peroxide.

Second Reagent

A reagent comprising cholesterol esterase, cholesterol oxidase, polyoxyethylene alkylamine or polyoxyethylene alkenylamine and a reagent for quantitatively determining hydrogen peroxide.

Kit 28

First Reagent

A reagent comprising a reagent for quantitatively determining hydrogen peroxide.

Second Reagent

A reagent comprising cholesterol esterase, cholesterol oxidase, polyoxyethylene polycyclic phenyl ether sulfate, polyoxyethylene alkylamine or polyoxyethylene alkenylamine and a reagent for quantitatively determining hydrogen peroxide.

In the kit for quantitatively determining HDL cholesterol according to the present invention, cholesterol esterase, cholesterol oxidase, cholesterol dehydrogenase, a nonionic surfactant, polyanion, albumin, a bile acid derivative, a reagent for quantitatively determining hydrogen peroxide, an oxidized coenzyme and a reagent for quantitatively determining a reduced coenzyme which are mentioned in the above-mentioned method for quantitatively determining HDL cholesterol according to the present invention may be used.

If necessary, the reagent and kit for quantitatively determining HDL cholesterol according to the present invention may further comprise the above-mentioned aqueous medium, stabilizing agent, antiseptic agent, interfering substance elimination agent, reaction promoter, and the like.

The reagent and kit for quantitatively determining HDL cholesterol according to the present invention may be in a form of the lyophilized state or in a state of being dissolved in an aqueous medium. When HDL cholesterol in a sample is measured using a reagent in a form of the lyophilized state, the reagent is dissolved in an aqueous medium prior to use, and the dissolved reagent is used for the measurement.

With regard to the amount of cholesterol esterase, cholesterol oxidase and cholesterol dehydrogenase in the reagent and kit for quantitatively determining HDL cholesterol according to the present invention, the amount that gives the concentration of the enzymes at 0.01 to 800 U/mL is preferred, and more preferably at 0.02 to 400 U/mL when dissolved in an aqueous medium. With regard to the amount of a nonionic surfactant in the reagent and kit for quantitatively determining HDL cholesterol according to the present invention, the amount that gives the concentration of the nonionic surfactant at 0.0001 to 10% is preferred, and more preferably at 0.001 to 5% when dissolved in an aqueous medium. With regard to the amount of polyanion in the reagent and kit for quantitatively determining HDL cholesterol according to the present invention, the amount that gives the concentration of polyanion at 0.001 to 10% is preferred, and more preferably at 0.01 to 5% when dissolved in an aqueous medium.

With regard to the amount of albumin in the reagent and kit for quantitatively determining of HDL cholesterol according to the present invention, the amount that gives the concentration of albumin at 0.001 to 10% is preferred, and more preferably at 0.01 to 5% when dissolved in an aqueous medium. With regard to the amount of a bile acid derivative in the reagent and kit for quantitatively determining of HDL cholesterol according to the present invention, the amount that gives the concentration of the bile acid derivative at 0.001 to 10%, is preferred is preferred, and more preferably at 0.01 to 5% when dissolved in an aqueous medium.

The present invention will now be illustrated in more detail in the following Examples, although they never intended to limit the scope of the present invention. Incidentally, in the present Examples, the following reagents and enzymes were used.

HEPES (manufactured by BDH Laboratory), EMSE (manufactured by Daito Chemix Corporation), sodium dextran sulfate (molecular weight: 500,000) (manufactured by Pharmacia), sodium dextran sulfate (molecular weight: 80,000) (manufactured by ICN), ι-carageenan (manufactured by Junsei Chemical), heparin lithium (manufactured by Wako Pure Chemical), sodium phosphotungstate (manufactured by Kanto Kagaku), bovine serum albumin (BSA; manufactured by Oriental Yeast), 4-aminoantipyrine (manufactured by Salkyo Kasei), peroxidase (manufactured by Toyobo), LPL311 (cholesterol esterase; manufactured by Toyobo), COO321 (cholesterol oxidase; manufactured by Toyobo), LPL6 (cholesterol esterase; Amano Enzyme), Nymeen L207 (polyoxyethylene dodecylamine; manufactured by NOF), Nymeen S204 (polyoxyethylene octadecylamine; manufactured by NOF), Nymeen S210 (polyoxyethylene octadecylamine; manufactured by NOF), Newcol OD420 (polyoxyethylene octadecylamine; manufactured by Nippon Nyukazai), Pionin D3104 (polyoxyethylene laurylamine; manufactured by Takemoto Yushi), Pionin D3110 (polyoxyethylene laurylamine; manufactured by Takemoto Yushi), Pionin D3605 [polhyoxyethylene alkyl(soybean)amine; manufactured by Takemoto Yushi], Newcol 2608F (polyoxyalkylene polycyclic phenyl ether; manufactured by Nippon Nyukazai), Nikkol R1020 (polyoxyethylene nonyl phenyl ether formaldehyde condensate; manufactured by Nikko Chemicals), AdekaPullulonic TR704 (ethylenediamine polyoxyethylene-polyoxypropylene condensate, Asahi Denka), Emulmin L90S (polyoxyethylene lauryl ether; manufactured by Sanyo Chemical Industries), sodium cholate (manufactured by Acros), sodium taurocholate (manufactured by Tokyo Kasei), sodium glycocholate (manufactured by Tokyo Kasei), Newcol 740-SF and Newcol 707-SF (both polyoxyethylene polycyclic phenyl ether sulfate; manufactured by Nippon Nyukazai).

BEST MODE FOR CARRYING OUT THE INVENTION

REFERENCE EXAMPLE 1

Preparation of Chemically Modified LPL311,

After LPL311 was added to a HEPES buffer (pH 8.5; 0.15 mol/L) to be 33 g/L and cooled to 5° C., Sanbright VFM-4101, Sanbright AKM-1510 or Sanbright MEAC-50HS (all manufactured by NFO) was added thereto to be 330 g/L and allowed to react for 3 hours. The resulting modified enzyme solution was not purified/separated but used as chemically modified LPL311 just as it was.

EXAMPLE 1

Kit for Quantitatively Determining HDL Cholesterol

A kit for quantitatively determining HDL cholesterol comprising the following first reagent and second reagent was prepared.

First Reagent (Reagent A)

| | |
|---|---|
| HEPES (pH 7.5) | 10 mmol/L |
| EMSE | 0.3 g/L |
| Sodium dextran sulfate (molecular weight: 500,000) | 1.0 g/L |
| BSA | 2.0 g/L |
| Nymeen L207 | 0.07 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

EXAMPLE 2

Kit for Quantitatively Determining HDL Cholesterol

A kit for quantitatively determining HDL cholesterol comprising the following first reagent and second reagent was prepared.

First Reagent (Reagent A)

| | |
|---|---|
| HEPES (pH 7.5) | 10 mmol/L |
| EMSE | 0.3 g/L |
| Sodium dextran sulfate (molecular weight: 500,000) | 1.0 g/L |
| BSA | 2.0 g/L |
| Nymeen L207 | 0.07 g/L |

Second Reagent (Reagent b)

| | |
|---|---|
| HEPES (pH 7.0) | 10 mmol/L |
| 4-Aminoantipyrine | 0.3 g/L |
| Peroxidase | 20 kU/L |
| Chemically modified LPL311 | 0.2 kU/L |
| COO321 | 3.0 kU/L |

EXAMPLE 3

Kit for Quantitatively Determining HDL Cholesterol

A kit for quantitatively determining HDL cholesterol comprising the following first reagent and second reagent was prepared.

First Reagent (Reagent A)

| | |
|---|---|
| HEPES (pH 7.5) | 10 mmol/L |
| EMSE | 0.3 g/L |
| Sodium dextran sulfate (molecular weight: 500,000) | 1.0 g/L |
| BSA | 2.0 g/L |
| Nymeen L207 | 0.07 g/L |

Second Reagent (Reagent c)

| | |
|---|---|
| HEPES (pH 7.0) | 10 mmol/L |
| 4-Aminoantipyrine | 0.3 g/L |
| Sodium cholate | 6.0 g/L |
| Peroxidase | 20 kU/L |
| LPL6 | 0.05 kU/L |
| COO321 | 3.0 kU/L |

EXAMPLE 4

Kit for Quantitatively Determining HDL Cholesterol

A kit for quantitatively determining HDL cholesterol comprising the following first reagent and second reagent was prepared.

First Reagent (Reagent A)

| | |
|---|---|
| HEPES (pH 7.5) | 10 mmol/L |
| EMSE | 0.3 g/L |
| Sodium dextran sulfate (molecular weight: 500,000) | 1.0 g/L |
| BSA | 2.0 g/L |
| Nymeen L207 | 0.07 g/L |

Second Reagent (Reagent d)

| | |
|---|---|
| HEPES (pH 7.0) | 10 mmol/L |
| 4-Aminoantipyrine | 0.3 g/L |
| Sodium cholate | 6.0 g/L |
| Peroxidase | 20 kU/L |
| Chemically modified LPL311 | 0.2 kU/L |
| COO321 | 3.0 kU/L |

COMPARATIVE EXAMPLE 1

Kit for Quantitatively Determining HDL Cholesterol

A kit for quantitatively determining HDL cholesterol comprising the following first reagent and second reagent was prepared.

First Reagent (Reagent B)

| | |
|---|---|
| HEPES (pH 7.5) | 10 mmol/L |
| EMSE | 0.3 g/L |
| BSA | 2.0 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

COMPARATIVE EXAMPLE 2

Kit for Quantitatively Determining HDL Cholesterol

A kit for quantitatively determining HDL cholesterol comprising the following first reagent and second reagent was prepared.

First Reagent (Reagent C)

| | |
|---|---|
| HEPES (pH 7.5) | 10 mmol/L |
| EMSE | 0.3 g/L |
| Sodium dextran sulfate (molecular weight: 500,000) | 1.0 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

COMPARATIVE EXAMPLE 3

Kit for Quantitatively Determining HDL Cholesterol

A kit for quantitatively determining HDL cholesterol comprising the following first reagent and second reagent was prepared.

First Reagent (Reagent D)

| | |
|---|---|
| HEPES (pH 7.5) | 10 mmol/L |
| EMSE | 0.3 g/L |
| Nymeen L207 | 0.07 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

COMPARATIVE EXAMPLE 4

Kit for Quantitatively Determining HDL Cholesterol

A kit for quantitatively determining HDL cholesterol comprising the following first reagent and second reagent was prepared.

First Reagent (Reagent E)

| | |
|---|---|
| HEPES (pH 7.5) | 10 mmol/L |
| EMSE | 0.3 g/L |
| Sodium dextran sulfate (molecular weight: 500,000) | 1.0 g/L |
| BSA | 2.0 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

COMPARATIVE EXAMPLE 5

Kit for Quantitatively Determining HDL Cholesterol

A kit for quantitatively determining HDL cholesterol comprising the following first reagent and second reagent was prepared.

First Reagent (Reagent F)

| | |
|---|---|
| HEPES (pH 7.5) | 10 mmol/L |
| EMSE | 0.3 g/L |
| BSA | 2.0 g/L |
| Nymeen L207 | 0.07 g/L |

Second Reagent (Reagent a)

| HEPES (pH 7.0) | 10 mmol/L |
|---|---|
| 4-Aminoantipyrine | 0.3 g/L |
| Peroxidase | 20 kU/L |
| LPL6 | 0.05 kU/L |
| COO321 | 3.0 kU/L |

COMPARATIVE EXAMPLE 6

Kit for Quantitatively Determining HDL Cholesterol

A kit for quantitatively determining HDL cholesterol comprising the following first reagent and second reagent was prepared.

First Reagent (Reagent G)

| HEPES (pH 7.5) | 10 mmol/L |
|---|---|
| EMSE | 0.3 g/L |
| Sodium dextran sulfate (molecular weight: 500,000) | 1.0 g/L |
| Nymeen L207 | 0.07 g/L |

Second Reagent (Reagent a)

| HEPES (pH 7.0) | 10 mmol/L |
|---|---|
| 4-Aminoantipyrine | 0.3 g/L |
| Peroxidase | 20 kU/L |
| LPL6 | 0.05 kU/L |
| COO321 | 3.0 kU/L |

EXAMPLE 5

Quantitative Determination of HDL Cholesterol

HDL cholesterol in 30 samples of human serum samples was measured by Hitachi 7170 autoanalyzer, using the kit of Example 1.

(1) Preparation of Calibration Curve

A calibration curve showing the relation between HDL cholesterol concentration and "absorbance" was prepared by Hitachi 7170 autoanalyzer, using a physiological brine (HDL cholesterol concentration: 0.0 mg/dL) and serum (HDL cholesterol concentration: 60.0 mg/dL) as standard solutions and the kit of Example 1 as a kit.

"Absorbance" used here means a value obtained by subtracting E1 from E2 on the basis of the two absorbances (E1 and E2) measured in the following reaction.

A standard solution (3 μL) and the first reagent (0.24 mL) were added to a reaction cell and heated at 37° C. for 5 minutes. After absorbance (E1) of the reaction solution was measured at a main wavelength of 600 nm and a sub-wavelength of 700 nm, the second reagent (0.08 mL) was added to the reaction solution, and the mixture was heated at 37° C. for 5 minutes. Absorbance (E2) of the reaction solution was measured at a main wavelength of 600 nm and a sub-wavelength of 700 nm.

(2) Calculation of "Absorbance" for a Human Serum Sample by the Reaction of the Sample with the Kit of Example 1

The same method as in the calculation of "absorbance" in (1) was conducted except that human serum sample was used instead of the standard solution used in the preparation of a calibration curve in (1) whereupon "absorbance" for the sample was calculated.

(3) Quantitative Determination of HDL Cholesterol Concentration in a Human Serum Sample HDL cholesterol concentration in each sample was determined by correlating the "absorbance" calculated in (2) and the calibration curve prepared in (1).

EXAMPLE 6

Quantitative Determination of HDL Cholesterol

The same operation as in the measuring method of Example 5 was conducted except that the kit of Example 2 was used instead of the kit of Example 1, whereupon HDL cholesterol in 40 human serum samples was measured by Hitachi 7170 autoanalyzer.

EXAMPLE 7

Quantitative Determination of HDL Cholesterol

The same operation as in the measuring method of Example 5 was conducted except that the kit of Example 3 was used instead of the kit of Example 1 whereupon HDL cholesterol in 40 human serum samples was measured by Hitachi 7170 autoanalyzer.

EXAMPLE 8

Quantitative Determination of HDL Cholesterol

The same operation as in the measuring method of Example 5 was conducted except that the kit of Example 4 was used instead of the kit of Example 1, whereupon HDL cholesterol in 40 human serum samples was measured by Hitachi 7170 autoanalyzer.

COMPARATIVE EXAMPLE 7

Quantitative Determination of HDL Cholesterol

The same operation as in the measuring method of Example 5 was conducted except that the kit of Comparative Example 1 was used instead of the kit of Example 1 whereupon HDL cholesterol in 40 human serum samples was measured by Hitachi 7170 autoanalyzer.

COMPARATIVE EXAMPLE 8

Quantitative Determination of HDL Cholesterol

The same operation as in the measuring method of Example 5 was conducted except that the kit of Comparative Example 2 was used instead of the kit of Example 1 whereupon HDL cholesterol in 40 human serum samples was measured by Hitachi 7170 autoanalyzer.

COMPARATIVE EXAMPLE 9

Quantitative Determination of HDL Cholesterol

The same operation as in the measuring method of Example 5 was conducted except that the kit of Comparative Example 3 was used instead of the kit of Example 1 whereupon HDL cholesterol in 40 human serum samples was measured by Hitachi 7170 autoanalyzer.

COMPARATIVE EXAMPLE 10

Quantitative Determination of HDL Cholesterol

The same operation as in the measuring method of Example 5 was conducted except that the kit of Comparative Example 4 was used instead of the kit of Example 1 whereupon HDL cholesterol in each of 40 human serum samples was measured by Hitachi 7170 autoanalyzer.

COMPARATIVE EXAMPLE 11

Quantitative Determination of HDL Cholesterol

The same operation as in the measuring method of Example 5 was conducted except that the kit of Comparative Example 5 was used instead of the kit of Example 1 whereupon HDL cholesterol in 40 human serum samples was measured by Hitachi 7170 autoanalyzer.

COMPARATIVE EXAMPLE 12

Quantitative Determination of HDL Cholesterol

The same operation as in the measuring method of Example 5 was conducted except that the kit of Comparative Example 6 was used instead of the kit of Example 1 whereupon HDL cholesterol in 40 human serum samples was measured by Hitachi 7170 autoanalyzer.

In the meanwhile, HDL cholesterol in the 40 human serum samples used in Examples 5 to 8 and Comparative Examples 7 to 12, was quantitatively determined according to a DCM (a Designated Comparison Method) mentioned in *Clinical Chemistry*, vol. 45, no. 10 (1999), and compared with each method.

Correlation coefficients between the methods of Examples 5 to 8 or Comparative Examples 7 to 12 and the DCM are shown in Table 1.

TABLE 1

| Method | Kit First Reagent | Kit Second Reagent | Correlation Coefficient |
|---|---|---|---|
| Example 5 | Reagent A | Reagent a | 0.960 |
| Example 6 | Reagent A | Reagent b | 0.958 |
| Example 7 | Reagent A | Reagent c | 0.983 |
| Example 8 | Reagent A | Reagent d | 0.996 |
| Comp. Ex. 7 | Reagent B | Reagent a | 0.590 |
| Comp. Ex. 8 | Reagent C | Reagent a | 0.385 |
| Comp. Ex. 9 | Reagent D | Reagent a | 0.388 |
| Comp. Ex. 10 | Reagent E | Reagent a | 0.800 |
| Comp. Ex. 11 | Reagent F | Reagent a | 0.405 |
| Comp. Ex. 12 | Reagent G | Reagent a | 0.118 |

Comp. Ex.: Comparative Example

From the comparison between Example 5 and Comparative Examples 7 to 12, it is proved that good correlation coefficient to the measurement by the DCM is obtained only in the measurement using a kit comprising all of BSA, sodium dextran sulfate and polyoxyethylene alkylamine besides enzymes for the measurement of cholesterol. From the comparison between Example 5 and Example 6, it is also proved that a good correlation coefficient to the measurement by a DCM is obtained in the measurement using a chemically modified cholesterol esterase. From the comparison between Example 5 and Example 7 and Example 6 and Example 8, it is also proved that a good correlation to the measurement by a DCM is obtained in the measurement using sodium cholate, a kind of a bile acid derivative in addition to enzymes for the measurement of cholesterol, BSA, sodium dextran sulfate and polyoxyethylene alkylamine.

EXAMPLE 9

Kit for Quantitatively Determining HDL Cholesterol

A kit for quantitatively determining HDL cholesterol comprising the following first reagent and second reagent was prepared.

First Reagent (Reagent H)

| | |
|---|---|
| HEPES (pH 7.5) | 10 mmol/L |
| EMSE | 0.3 g/L |
| Sodium dextran sulfate (molecular weight: 80,000) | 0.5 g/L |
| BSA | 2.0 g/L |
| Nymeen L207 | 0.07 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

EXAMPLE 10

Kit for Quantitatively Determining HDL Cholesterol

A kit for quantitatively determining HDL cholesterol comprising the following first reagent and second reagent was prepared.

First Reagent (Reagent I)

| | |
|---|---|
| HEPES (pH 7.5) | 10 mmol/L |
| EMSE | 0.3 g/L |
| ι-carageenan | 0.5 g/L |
| BSA | 2.0 g/L |
| Nymeen L207 | 0.07 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

EXAMPLE 11

Kit for Quantitatively Determining HDL Cholesterol

A kit for quantitatively determining HDL cholesterol comprising the following first reagent and second reagent was prepared.

First Reagent (Reagent J)

| | |
|---|---|
| HEPES (pH 7.5) | 10 mmol/L |
| EMSE | 0.3 g/L |
| Heparin lithium | 0.5 g/L |
| BSA | 2.0 g/L |
| Nymeen L207 | 0.07 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

EXAMPLE 12

Kit for Quantitatively, Determining HDL Cholesterol

A kit for quantitatively determining HDL cholesterol comprising the following first reagent and second reagent was prepared.

First Reagent (Reagent K)

| | |
|---|---|
| HEPES (pH 7.5) | 10 mmol/L |
| EMSE | 0.3 g/L |
| Sodium phosphotungstate | 0.5 g/L |
| BSA | 2.0 g/L |
| Nymeen L207 | 0.07 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

EXAMPLE 13

Quantitative Determination of HDL Cholesterol

The same operation as in the measuring method of Example 5 was conducted except that the kit of Example 9 was used instead of the kit of Example 1 whereupon HDL cholesterol in 40 human serum samples was measured by Hitachi 7170 autoanalyzer.

EXAMPLE 14

Quantitative Determination of HDL Cholesterol

The same operation as in the measuring method of Example 5 was conducted except that the kit of Example 10 was used instead of the kit of Example 1 whereupon HDL cholesterol in 40 human serum samples was measured by Hitachi 7170 autoanalyzer.

EXAMPLE 15

Quantitative Determination of HDL Cholesterol

The same operation as in the measuring method of Example 5 was conducted except that the kit of Example 11 was used instead of the kit of Example 1 whereupon HDL cholesterol in 40 human serum samples was measured by Hitachi 7170 autoanalyzer.

EXAMPLE 16

Quantitative Determination of HDL Cholesterol

The same operation as in the measuring method of Example 5 was conducted except that the kit of Example 12 was used instead of the kit of Example 1 whereupon HDL cholesterol in 40 human serum samples was measured by Hitachi 7170 autoanalyzer.

Correlation coefficients between the DCM and the measuring methods of Examples 13 to 16 are shown in Table 2.

TABLE 2

| | Kit | | Correlation |
|---|---|---|---|
| Method | First Reagent | Second Regent | Coefficient |
| Example 13 | Reagent H | Reagent a | 0.995 |
| Example 14 | Reagent I | Reagent a | 0.988 |
| Example 15 | Reagent J | Reagent a | 0.986 |
| Example 16 | Reagent K | Reagent a | 0.983 |

From the comparison between Example 5 and Examples 13 to 16, it is also proved that a good correlation coefficient to the measurement by a DCM is obtained in the measurements using polyanion other than sodium dextran sulfate (molecular weight: 500,000).

EXAMPLE 17

Kit for Quantitatively Determining HDL Cholesterol

A kit for quantitatively determining HDL cholesterol comprising the following first reagent and second reagent was prepared.

First Reagent (Reagent L)

| | |
|---|---|
| HEPES (pH 7.5) | 10 mmol/L |
| EMSE | 0.3 g/L |
| Sodium dextran sulfate (molecular weight: 500,000) | 1.0 g/L |

-continued

| | |
|---|---|
| BSA | 2.0 g/L |
| Newcol OD420 | 0.05 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

EXAMPLE 18

Kit for Quantitatively Determining HDL Cholesterol

A kit for quantitatively determining HDL cholesterol comprising the following first reagent and second reagent was prepared.

First Reagent (Reagent M)

| | |
|---|---|
| HEPES (pH 7.5) | 10 mmol/L |
| EMSE | 0.3 g/L |
| Sodium dextran sulfate (molecular weight: 500,000) | 1.0 g/L |
| BSA | 2.0 g/L |
| Pionin D3065 | 0.01 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

EXAMPLE 19

Kit for Quantitatively Determining HDL Cholesterol

A kit for quantitatively determining HDL cholesterol comprising the following first reagent and second reagent was prepared.

First Reagent (Reagent N)

| | |
|---|---|
| HEPES (pH 7.5) | 10 mmol/L |
| EMSE | 0.3 g/L |
| Sodium dextran sulfate (molecular weight: 500,000) | 1.0 g/L |
| BSA | 2.0 g/L |
| Emulmin L90S | 0.05 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

EXAMPLE 20

Kit for Quantitatively Determining HDL Cholesterol

A kit for quantitatively determining HDL cholesterol comprising the following first reagent and second reagent was prepared.

First Reagent (Reagent O)

| | |
|---|---|
| HEPES (pH 7.5) | 10 mmol/L |
| EMSE | 0.3 g/L |
| Sodium dextran sulfate (molecular weight: 500,000) | 1.0 g/L |
| BSA | 2.0 g/L |
| Newcol 2608F | 0.2 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

EXAMPLE 21

Kit for Quantitatively Determining HDL Cholesterol

A kit for quantitatively determining HDL cholesterol comprising the following first reagent and second reagent was prepared.

First Reagent (Reagent P)

| | |
|---|---|
| HEPES (pH 7.5) | 10 mmol/L |
| EMSE | 0.3 g/L |
| Sodium dextran sulfate (molecular weight: 500,000) | 1.0 g/L |
| BSA | 2.0 g/L |
| Nikkol R1020 | 0.2 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

EXAMPLE 22

Kit for Quantitatively Determining HDL Cholesterol

A kit for quantitatively determining HDL cholesterol comprising the following first reagent and second reagent was prepared.

First Reagent (Reagent Q)

| | |
|---|---|
| HEPES (pH 7.5) | 10 mmol/L |
| EMSE | 0.3 g/L |
| Sodium dextran sulfate (molecular weight: 500,000) | 1.0 g/L |
| BSA | 2.0 g/L |
| Adeka Pullulonic RT704 | 1.5 g/L |

Second Reagent (Reagent a)

| | |
|---|---|
| HEPES (pH 7.0) | 10 mmol/L |
| 4-Aminoantipyrine | 0.3 g/L |
| Peroxidase | 20 kU/L |
| LPL6 | 0.05 kU/L |
| COO321 | 3.0 kU/L |

EXAMPLE 23

Kit for Quantitatively Determining HDL Cholesterol

A kit for quantitatively determining HDL cholesterol comprising the following first reagent and second reagent was prepared.

First Reagent (Reagent Q)

| | |
|---|---|
| HEPES (pH 7.5) | 10 mmol/L |
| EMSE | 0.3 g/L |
| Sodium dextran sulfate (molecular weight: 500,000) | 1.0 g/L |
| BSA | 2.0 g/L |
| Adeka Pullulonic TR704 | 1.5 g/L |

Second Reagent (Reagent b)

| | |
|---|---|
| HEPES (pH 7.0) | 10 mmol/L |
| 4-Aminoantipyrine | 0.3 g/L |
| Peroxidase | 20 kU/L |
| Chemically modified LPL311 | 0.2 kU/L |
| COO321 | 3.0 kU/L |

EXAMPLE 24

Quantitative Determination of HDL Cholesterol

The same operation as in the measuring method of Example 5 was conducted except that the kit of Example 17 was used instead of the kit of Example 1 whereupon HDL cholesterol in 40 human serum samples was measured by Hitachi 7170 autoanalyzer.

EXAMPLE 25

Quantitative Determination of HDL Cholesterol

The same operation as in the measuring method of Example 5 was conducted except that the kit of Example 18 was used instead of the kit of Example 1 whereupon HDL cholesterol in 40 human serum samples was measured by Hitachi 7170 autoanalyzer.

EXAMPLE 26

Quantitative Determination of HDL Cholesterol

The same operation as in the measuring method of Example 5 was conducted except that the kit of Example 19 was used instead of the kit of Example 1 whereupon HDL cholesterol in 40 human serum sample s was measured by Hitachi 7170 autoanalyzer.

EXAMPLE 27

Quantitative Determination of HDL Cholesterol

The same operation as in the measuring method of Example 5 was conducted except that the kit of Example 20 was used instead of the kit of Example 1 whereupon HDL cholesterol in 40 human serum samples was measured by Hitachi 7170 autoanalyzer.

EXAMPLE 28

Quantitative Determination of HDL Cholesterol

The same operation as in the measuring method of Example 5 was conducted except that the kit of Example 21 was used instead of the kit of Example 1 whereupon HDL cholesterol in 40 human serum samples was measured by Hitachi 7170 autoanalyzer.

EXAMPLE 29

Quantitative Determination of HDL Cholesterol

The same operation as in the measuring method of Example 5 was conducted except that the kit of Example 22 was used instead of the kit of Example 1 whereupon HDL cholesterol in 40 human serum samples was measured by Hitachi 7170 autoanalyzer.

EXAMPLE 30

Quantitative Determination of HDL Cholesterol

The same operation as in the measuring method of Example 5 was conducted except that the kit of Example 23 was used instead of the kit of Example 1 whereupon HDL cholesterol in 40 human serum samples was measured by Hitachi 7170 autoanalyzer.

Correlation coefficients between DCM and the measuring methods of Examples 24 to 30 are shown in Table 3.

TABLE 3

| Method | Kit | | Correlation Coefficient |
| --- | --- | --- | --- |
| | First Reagent | Second Reagent | |
| Example 24 | Reagent L | Reagent a | 0.984 |
| Example 25 | Reagent M | Reagent a | 0.909 |
| Example 26 | Reagent N | Reagent a | 0.934 |
| Example 27 | Reagent O | Reagent a | 0.952 |
| Example 28 | Reagent P | Reagent a | 0.949 |
| Example 29 | Reagent Q | Reagent a | 0.913 |
| Example 30 | Reagent Q | Reagent b | 0.993 |

As same as in Example 5, it is also proved that a good correlation coefficient to the measurement by a DCM is obtained in the measurements using nonionic surfactants other than Nymeen L207 (polyoxyethylene dodecylamine). In addition, from the comparison between Example 29 and Examples 30, it is proved that a good correlation coefficient to the measurement by a DCM is obtained in the measurement using a chemically modified cholesterol esterase.

EXAMPLE 31

Kit for Quantitatively Determining HDL Cholesterol

A kit for quantitatively determining HDL cholesterol comprising the following first reagent and second reagent was prepared.

First Reagent (Reagent R)

| HEPES (pH 7.5) | 10 mmol/L |
| --- | --- |
| EMSE | 0.3 g/L |
| Sodium taurocholate | 2.7 g/L |

Second Reagent (Reagent e)

| HEPES (pH 7.0) | 10 mmol/L |
| --- | --- |
| 4-Aminoantipyrine | 0.3 g/L |
| Pionin D3104 | 0.05 g/L |
| Peroxidase | 20 kU/L |
| Chemically modified LPL311 | 0.2 kU/L |
| COO321 | 3.0 kU/L |

EXAMPLE 32

Kit for Quantitatively Determining HDL Cholesterol

A kit for quantitatively determining HDL cholesterol comprising the following first reagent and second reagent was prepared.

First Reagent (Reagent R)

| HEPES (pH 7.5) | 10 mmol/L |
| --- | --- |
| EMSE | 0.3 g/L |
| Sodium taurocholate | 2.7 g/L |

Second Reagent (Reagent f)

| HEPES (pH 7.0) | 10 mmol/L |
| --- | --- |
| 4-Aminoantipyrine | 0.3 g/L |
| Nymeen S204 | 0.05 g/L |
| Peroxidase | 20 kU/L |
| Chemically modified LPL311 | 0.2 kU/L |
| COO321 | 3.0 kU/L |

EXAMPLE 33

Kit for Quantitatively Determining HDL Cholesterol

A kit for quantitatively determining HDL cholesterol comprising the following first reagent and second reagent was prepared.

First Reagent (Reagent R)

| HEPES (pH 7.5) | 10 mmol/L |
| --- | --- |
| EMSE | 0.3 g/L |
| Sodium taurocholate | 2.7 g/L |

Second Reagent (Reagent g)

| HEPES (pH 7.0) | 10 mmol/L |
| --- | --- |
| 4-Aminoantipyrine | 0.3 g/L |
| Nymeen S210 | 0.05 g/L |
| Peroxidase | 20 kU/L |
| Chemically modified LPL311 | 0.2 kU/L |
| COO321 | 3.0 kU/L |

EXAMPLE 34

Kit for Quantitatively Determining HDL Cholesterol

A kit for quantitatively determining HDL cholesterol comprising the following first reagent and second reagent was prepared.

First Reagent (Reagent S)

| HEPES (pH 7.5) | 10 mmol/L |
| --- | --- |
| EMSE | 0.3 g/L |
| Sodium cholate | 2.0 g/L |

Second Reagent (Reagent g)

| HEPES (pH 7.0) | 10 mmol/L |
| --- | --- |
| 4-Aminoantipyrine | 0.3 g/L |
| Nymeen S210 | 0.05 g/L |
| Peroxidase | 20 kU/L |
| Chemically modified LPL311 | 0.2 kU/L |
| COO321 | 3.0 kU/L |

EXAMPLE 35

Kit for Quantitatively Determining HDL Cholesterol

A kit for quantitatively determining HDL cholesterol comprising the following first reagent and second reagent was prepared.

First Reagent (Reagent T)

| | |
|---|---|
| HEPES (pH 7.5) | 10 mmol/L |
| EMSE | 0.3 g/L |
| Sodium glycocholate | 2.4 g/L |

Second Reagent (Reagent g)

| | |
|---|---|
| HEPES (pH 7.0) | 10 mmol/L |
| 4-Aminoantipyrine | 0.3 g/L |
| Nymeen S210 | 0.05 g/L |
| Peroxidase | 20 kU/L |
| Chemically modified LPL311 | 0.2 kU/L |
| COO321 | 3.0 kU/L |

EXAMPLE 36

Kit for Quantitatively Determining HDL Cholesterol

A kit for quantitatively determining HDL cholesterol comprising the following first reagent and second reagent was prepared.

First Reagent (Reagent D)

| | |
|---|---|
| HEPES (pH 7.5) | 10 mmol/L |
| EMSE | 0.3 g/L |
| Nymeen S207 | 0.07 g/L |

Second Reagent (Reagent d)

| | |
|---|---|
| HEPES (pH 7.0) | 10 mmol/L |
| 4-Aminoantipyrine | 0.3 g/L |
| Sodium cholate | 6.0 g/L |
| Peroxidase | 20 kU/L |
| Chemically modified LPL311 | 0.2 kU/L |
| COO321 | 3.0 kU/L |

EXAMPLE 37

Kit for Quantitatively Determining HDL Cholesterol

A kit for quantitatively determining HDL cholesterol comprising the following first reagent and second reagent was prepared.

First Reagent (Reagent F)

| | |
|---|---|
| HEPES (pH 7.5) | 10 mmol/L |
| EMSE | 0.3 g/L |
| BSA | 2.0 g/L |
| Nymeen S207 | 0.07 g/L |

Second Reagent (Reagent d)

| | |
|---|---|
| HEPES (pH 7.0) | 10 mmol/L |
| 4-Aminoantipyrine | 0.3 g/L |
| Sodium cholate | 6.0 g/L |
| Peroxidase | 20 kU/L |
| Chemically modified LPL311 | 0.2 kU/L |
| COO321 | 3.0 kU/L |

EXAMPLE 38

Kit for Quantitatively Determining HDL Cholesterol

A kit for quantitatively determining HDL cholesterol comprising the following first reagent and second reagent was prepared.

First Reagent (Reagent G)

| | |
|---|---|
| HEPES (pH 7.5) | 10 mmol/L |
| EMSE | 0.3 g/L |

Sodium dextran sulfate (molecular weight: 500,000) 1.0 g/L

Nymeen S207 0.07 g/L

Second Reagent (Reagent d)

| | |
|---|---|
| HEPES (pH 7.0) | 10 mmol/L |
| 4-Aminoantipyrine | 0.3 g/L |
| Sodium cholate | 6.0 g/L |
| Peroxidase | 20 kU/L |
| Chemically modified LPL311 | 0.2 kU/L |
| COO321 | 3.0 kU/L |

COMPARATIVE EXAMPLE 13

Kit for Quantitatively Determining HDL Cholesterol

A kit for quantitatively determining HDL cholesterol comprising the following first reagent and second reagent was prepared.

First Reagent (Reagent R)

| | |
|---|---|
| HEPES (pH 7.5) | 10 mmol/L |
| EMSE | 0.3 g/L |
| Sodium taurocholate | 2.7 g/L |

Second Reagent (Reagent b)

| | |
|---|---|
| HEPES (pH 7.0) | 10 mmol/L |
| 4-Aminoantipyrine | 0.3 g/L |
| Peroxidase | 20 kU/L |
| Chemically modified LPL311 | 0.2 kU/L |
| COO321 | 3.0 kU/L |

COMPARATIVE EXAMPLE 14

Kit for Quantitatively Determining HDL Cholesterol

A kit for quantitatively determining HDL cholesterol comprising the following first reagent and second reagent was prepared.

First Reagent (Reagent S)

| | |
|---|---|
| HEPES (pH 7.5) | 10 mmol/L |
| EMSE | 0.3 g/L |
| Sodium cholate | 2.0 g/L |

Second Reagent (Reagent b)

| | |
|---|---|
| HEPES (pH 7.0) | 10 mmol/L |
| 4-Aminoantipyrine | 0.3 g/L |
| Peroxidase | 20 kU/L |
| Chemically modified LPL311 | 0.2 kU/L |
| COO321 | 3.0 kU/L |

COMPARATIVE EXAMPLE 15

Kit for Quantitatively Determining HDL Cholesterol

A kit for quantitatively determining HDL cholesterol comprising the following first reagent and second reagent was prepared.

First Reagent (Reagent T)

| | |
|---|---|
| HEPES (pH 7.5) | 10 mmol/L |
| EMSE | 0.3 g/L |
| Sodium glycocholate | 2.4 g/L |

Second Reagent (Reagent b)

| | |
|---|---|
| HEPES (pH 7.0) | 10 mmol/L |
| 4-Aminoantipyrine | 0.3 g/L |
| Peroxidase | 20 kU/L |
| Chemically modified LPL311 | 0.2 kU/L |
| COO321 | 3.0 kU/L |

COMPARATIVE EXAMPLE 16

Kit for Quantitatively Determining HDL Cholesterol

A kit for quantitatively determining HDL cholesterol comprising the following first reagent and second reagent was prepared.

First Reagent (Reagent U)

| | |
|---|---|
| HEPES (pH 7.5) | 10 mmol/L |
| EMSE | 0.3 g/L |

Second Reagent (Reagent e)

| | |
|---|---|
| HEPES (pH 7.0) | 10 mmol/L |
| 4-Aminoantipyrine | 0.3 g/L |
| Pionin D3104 | 0.05 g/L |
| Peroxidase | 20 kU/L |
| Chemically modified LPL311 | 0.2 kU/L |
| COO321 | 3.0 kU/L |

COMPARATIVE EXAMPLE 17

Kit for Quantitatively Determining HDL Cholesterol

A kit for quantitatively determining HDL cholesterol comprising the following first reagent and second reagent was prepared.

First Reagent (Reagent U)

| | |
|---|---|
| HEPES (pH 7.5) | 10 mmol/L |
| EMSE | 0.3 g/L |

Second Reagent (Reagent f)

| | |
|---|---|
| HEPES (pH 7.0) | 10 mmol/L |
| 4-Aminoantipyrine | 0.3 g/L |
| Nymeen S204 | 0.05 g/L |
| Peroxidase | 20 kU/L |
| Chemically modified LPL311 | 0.2 kU/L |
| COO321 | 3.0 kU/L |

COMPARATIVE EXAMPLE 18

Kit for Quantitatively Determining HDL Cholesterol

A kit for quantitatively determining HDL cholesterol comprising the following first reagent and second reagent was prepared.

First Reagent (Reagent U)

| | |
|---|---|
| HEPES (pH 7.5) | 10 mmol/L |
| EMSE | 0.3 g/L |

Second Reagent (Reagent g)

| | |
|---|---|
| HEPES (pH 7.0) | 10 mmol/L |
| 4-Aminoantipyrine | 0.3 g/L |
| Nymeen S210 | 0.05 g/L |
| Peroxidase | 20 kU/L |
| Chemically modified LPL311 | 0.2 kU/L |
| COO321 | 3.0 kU/L |

EXAMPLE 39

Quantitative Determination of HDL Cholesterol

The same operation as in the measuring method of Example 5 was conducted except that the kit of Example 31 was used instead of the kit of Example 1 whereupon HDL cholesterol in 40 human serum samples was measured by Hitachi 7170 autoanalyzer.

EXAMPLE 40

Quantitative Determination of HDL Cholesterol

The same operation as in the measuring method of Example 5 was conducted except that the kit of Example 32 was used instead of the kit of Example 1 whereupon HDL cholesterol in 40 human serum samples was measured by Hitachi 7170 autoanalyzer.

EXAMPLE 41

Quantitative Determination of HDL Cholesterol

The same operation as in the measuring method of Example 5 was conducted except that the kit of Example 33 was used instead of the kit of Example 1 whereupon HDL cholesterol in 40 human serum samples was measured by Hitachi 7170 autoanalyzer.

EXAMPLE 42

Quantitative Determination of HDL Cholesterol

The same operation as in the measuring method of Example 5 was conducted except that the kit of Example 34 was used instead of the kit of Example 1 whereupon HDL cholesterol in 40 human serum samples was measured by Hitachi 7170 autoanalyzer.

EXAMPLE 43

Quantitative Determination of HDL Cholesterol

The same operation as in the measuring method of Example 5 was conducted except that the kit of Example 35 was used instead of the kit of Example 1 whereupon HDL cholesterol in 40 human serum samples was measured by Hitachi 7170 autoanalyzer.

EXAMPLE 44

Quantitative Determination of HDL Cholesterol

The same operation as in the measuring method of Example 5 was conducted except that the kit of Example 36 was used instead of the kit of Example 1 whereupon HDL cholesterol in 40 human serum samples was measured by Hitachi 7170 autoanalyzer.

EXAMPLE 45

Quantitative Determination of HDL Cholesterol

The same operation as in the measuring method of Example 5 was conducted except that the kit of Example 37 was used instead of the kit of Example 1 whereupon HDL cholesterol in 40 human serum samples was measured by Hitachi 7170 autoanalyzer.

EXAMPLE 46

Quantitative Determination of HDL Cholesterol

The same operation as in the measuring method of Example 5 was conducted except that the kit of Example 38 was used instead of the kit of Example 1 whereupon HDL cholesterol in 40 human serum samples was measured by Hitachi 7170 autoanalyzer.

COMPARATIVE EXAMPLE 19

Quantitative Determination of HDL Cholesterol

The same operation as in the measuring method of Example 5 was conducted except that the kit of Comparative Example 13 was used instead of the kit of Example 1 whereupon HDL cholesterol in 40 human serum samples was measured by Hitachi 7170 autoanalyzer.

COMPARATIVE EXAMPLE 20

Quantitative Determination of HDL Cholesterol

The same operation as in the measuring method of Example 5 was conducted except that the kit of Comparative Example 14 was used instead of the kit of Example 1 whereupon HDL cholesterol in 40 human serum samples was measured by Hitachi 7170 autoanalyzer.

COMPARATIVE EXAMPLE 21

Quantitative Determination of HDL Cholesterol

The same operation as in the measuring method of Example 5 was conducted except that the kit of Comparative Example 15 was used instead of the kit of Example 1 whereupon HDL cholesterol in each of 40 human serum samples was measured by Hitachi 7170 autoanalyzer.

COMPARATIVE EXAMPLE 22

Quantitative Determination of HDL Cholesterol

The same operation as in the measuring method of Example 5 was conducted except that the kit of Comparative Example 16 was used instead of the kit of Example 1 whereupon HDL cholesterol in 40 human serum samples was measured by Hitachi 7170 autoanalyzer.

COMPARATIVE EXAMPLE 23

Quantitative Determination of HDL Cholesterol

The same operation as in the measuring method of Example 5 was conducted except that the kit of Comparative Example 17 was used instead of the kit of Example 1 whereuon HDL cholesterol in 40 human serum samples was measured by Hitachi 7170 autoanalyzer.

COMPARATIVE EXAMPLE 24

Quantitative Determination of HDL Cholesterol

The same operation as in the measuring method of Example 5 was conducted except that the kit of Comparative Example 18 was used instead of the kit of Example 1 whereupon HDL cholesterol in 40 human serum samples was measured by Hitachi 7170 autoanalyzer.

Correlation coefficients between the DCM and the measuring methods of Examples 39 to 46 or Comparative Examples 19 to 24 are shown in Table 4.

TABLE 4

| Method | Kit First Reagent | Kit Second Reagent | Correlation Coefficient |
|---|---|---|---|
| Example 39 | Reagent R | Reagent e | 0.992 |
| Example 40 | Reagent R | Reagent f | 0.986 |
| Example 41 | Reagent R | Reagent g | 0.994 |
| Example 42 | Reagent S | Reagent g | 0.994 |
| Example 43 | Reagent T | Reagent g | 0.993 |
| Example 44 | Reagent D | Reagent d | 0.978 |
| Example 45 | Reagent F | Reagent d | 0.988 |
| Example 46 | Reagent G | Reagent d | 0.984 |
| Example 19 | Reagent R | Reagent b | 0.967 |
| Example 20 | Reagent S | Reagent b | 0.975 |
| Example 21 | Reagent T | Reagent b | 0.976 |
| Example 22 | Reagent U | Reagent e | 0.634 |
| Example 23 | Reagent U | Reagent f | 0.665 |
| Example 24 | Reagent U | Reagent g | 0.884 |

From the comparison between Examples 39 to 43 and Comparative Examples 19 to 24, it is proved that the measurement using kits comprising both of an anionic bile acid derivative and polyoxyethylene alkylamine correlates better to the measurement by a DCM than the measurement using kits comprising only one of an anionic bile acid derivative and polyoxyethylene alkylamine. Furthermore, from the comparison between Example 44 and Examples 45 to 46, it is also proved that a good correlation coefficient to the measurement by a DCM is observed in the measurement using kits comprising dextran sulfate or albumin in addition to enzymes for the measurement of cholesterol, an anionic bile acid derivative and polyoxyethylene alkylamine.

EXAMPLE 47

Kit for Quantitatively Determining HDL Cholesterol

A kit for quantitatively determining HDL cholesterol comprising the following first reagent and second reagent was prepared.

First Reagent (Reagent V)

| | |
|---|---|
| HEPES (pH 7.5) | 10 mmol/L |
| EMSE | 0.3 g/L |
| Newcol 740 SF | 0.5 g/L |

Second Reagent (Reagent h)

| | |
|---|---|
| HEPES (pH 7.0) | 10 mmol/L |
| 4-Aminoantipyrine | 0.3 g/L |
| Pionin D3110 | 0.3 g/L |
| Peroxidase | 20 kU/L |
| Chemically modified LPL311 | 0.2 kU/L |
| COO321 | 3.0 kU/L |

EXAMPLE 48

Kit for Quantitatively Determining HDL Cholesterol

A kit for quantitatively determining HDL cholesterol comprising the following first reagent and second reagent was prepared.

First Reagent (Reagent W)

| | |
|---|---|
| HEPES (pH 7.5) | 10 mmol/L |
| EMSE | 0.3 g/L |
| Newcol 707SF | 0.5 g/L |

Second Reagent (Reagent i)

| | |
|---|---|
| HEPES (pH 7.0) | 10 mmol/L |
| 4-Aminoantipyrine | 0.3 g/L |
| Nymeen L207 | 0.1 g/L |
| Peroxidase | 20 kU/L |
| Chemically modified LPL311 | 0.2 kU/L |
| COO321 | 3.0 kU/L |

EXAMPLE 49

Kit for Quantitatively Determining HDL Cholesterol

A kit for quantitatively determining HDL cholesterol comprising the following first reagent and second reagent was prepared.

First Reagent (Reagent W)

| | |
|---|---|
| HEPES (pH 7.5) | 10 mmol/L |
| EMSE | 0.3 g/L |
| Newcol 707SF | 0.5 g/L |

Second Reagent (Reagent h)

| | |
|---|---|
| HEPES (pH 7.0) | 10 mmol/L |
| 4-Aminoantipyrine | 0.3 g/L |
| Pionin D3110 | 0.3 g/L |
| Peroxidase | 20 kU/L |
| Chemically modified LPL311 | 0.2 kU/L |
| COO321 | 3.0 kU/L |

EXAMPLE 50

Kit for Quantitatively Determining HDL Cholesterol

A kit for quantitatively determining HDL cholesterol comprising the following first reagent and second reagent was prepared.

First Reagent (Reagent X)

| | |
|---|---|
| HEPES (pH 7.5) | 10 mmol/L |
| EMSE | 0.3 g/L |
| Sodium dextran sulfate (molecular weight: 500,000) | 1.0 g/L |
| Newcol 707SF | 0.5 g/L |

Second Reagent (Reagent h)

| | |
|---|---|
| HEPES (pH 7.0) | 10 mmol/L |
| 4-Aminoantipyrine | 0.3 g/L |
| Pionin D3110 | 0.3 g/L |
| Peroxidase | 20 kU/L |
| Chemically modified LPL311 | 0.2 kU/L |
| COO321 | 3.0 kU/L |

EXAMPLE 51

Kit for Quantitatively Determining HDL Cholesterol

A kit for quantitatively determining HDL cholesterol comprising the following first reagent and second reagent was prepared.

First Reagent (Reagent Y)

| | |
|---|---|
| HEPES (pH 7.5) | 10 mmol/L |
| EMSE | 0.3 g/L |
| BSA | 2.0 g/L |
| Newcol 707SF | 0.5 g/L |

Second Reagent (Reagent h)

| | |
|---|---|
| HEPES (pH 7.0) | 10 mmol/L |
| 4-Aminoantipyrine | 0.3 g/L |
| Pionin D3110 | 0.3 g/L |
| Peroxidase | 20 kU/L |
| Chemically modified LPL311 | 0.2 kU/L |
| COO321 | 3.0 kU/L |

EXAMPLE 52

Kit for Quantitatively Determining HDL Cholesterol

A kit for quantitatively determining HDL cholesterol comprising the following first reagent and second reagent was prepared.

First Reagent (Reagent Z)

| | |
|---|---|
| HEPES (pH 7.5) | 10 mmol/L |
| EMSE | 0.3 g/L |
| Sodium dextran sulfate (molecular weight: 500,000) | 1.0 g/L |
| BSA | 2.0 g/L |
| Newcol 707SF | 0.5 g/L |

Second Reagent (Reagent h)

| | |
|---|---|
| HEPES (pH 7.0) | 10 mmol/L |
| 4-Aminoantipyrine | 0.3 g/L |
| Pionin D3110 | 0.3 g/L |
| Peroxidase | 20 kU/L |
| Chemically modified LPL311 | 0.2 kU/L |
| COO321 | 3.0 kU/L |

COMPARATIVE EXAMPLE 25

Kit for Quantitatively Determining HDL Cholesterol

A kit for quantitatively determining HDL cholesterol comprising the following first reagent and second reagent was prepared.

First Reagent (Reagent V)

| | |
|---|---|
| HEPES (pH 7.5) | 10 mmol/L |
| EMSE | 0.3 g/L |
| Newcol 740SF | 0.5 g/L |

Second Reagent (Reagent b)

| | |
|---|---|
| HEPES (pH 7.0) | 10 mmol/L |
| 4-Aminoantipyrine | 0.3 g/L |
| Peroxidase | 20 kU/L |
| Chemically modified LPL311 | 0.2 kU/L |
| COO321 | 3.0 kU/L |

COMPARATIVE EXAMPLE 26

Kit for Quantitatively Determining HDL Cholesterol

A kit for quantitatively determining HDL cholesterol comprising the following first reagent and second reagent was prepared.

First Reagent (Reagent W)

| | |
|---|---|
| HEPES (pH 7.5) | 10 mmol/L |
| EMSE | 0.3 g/L |
| Newcol 707SF | 0.5 g/L |

Second Reagent (Reagent b)

| | |
|---|---|
| HEPES (pH 7.0) | 10 mmol/L |
| 4-Aminoantipyrine | 0.3 g/L |
| Peroxidase | 20 kU/L |
| Chemically modified LPL311 | 0.2 kU/L |
| COO321 | 3.0 kU/L |

COMPARATIVE EXAMPLE 27

Kit for Quantitatively Determining HDL Cholesterol

A kit for quantitatively determining HDL cholesterol comprising the following first reagent and second reagent was prepared.

First Reagent (Reagent U)

| | |
|---|---|
| HEPES (pH 7.5) | 10 mmol/L |
| EMSE | 0.3 g/L |

Second Reagent (Reagent h)

| | | |
|---|---|---|
| HEPES (pH 7.0) | 10 | mmol/L |
| 4-Aminoantipyrine | 0.3 | g/L |
| Pionin D3110 | 0.3 | g/L |
| Peroxidase | 20 | kU/L |
| Chemically modified LPL311 | 0.2 | kU/L |
| COO321 | 3.0 | kU/L |

EXAMPLE 53

Quantitative Determination of HDL Cholesterol

By the same operation as in the measuring method of Example 5 except that the kit of Example 47 was used instead of the kit of Example 1, concentration of HDL cholesterol in each of 40 human serum samples was measured on Hitachi 7170 autoanalyzer.

EXAMPLE 54

Quantitative Determination of HDL Cholesterol

By the same operation as in the measuring method of Example 5 except that the kit of Example 48 was used instead of the kit of Example 1, concentration of HDL cholesterol in each of 40 human serum samples was measured on Hitachi 7170 autoanalyzer.

EXAMPLE 55

Quantitative Determination of HDL Cholesterol

By the same operation as in the measuring method of Example 5 except that the kit of Example 49 was used instead of the kit of Example 1, concentration of HDL cholesterol in each of 40 human serum samples was measured on Hitachi 7170 autoanalyzer.

EXAMPLE 56

Quantitative Determination of HDL Cholesterol

By the same operation as in the measuring method of Example 5 except that the kit of Example 50 was used instead of the kit of Example 1, concentration of HDL cholesterol in each of 40 human serum samples was measured on Hitachi 7170 autoanalyzer.

EXAMPLE 57

Quantitative Determination of HDL Cholesterol

By the same operation as in the measuring method of Example 5 except that the kit of Example 51 was used instead of the kit of Example 1, concentration of HDL cholesterol in each of 40 human serum samples was measured on Hitachi 7170 autoanalyzer.

EXAMPLE 58

Quantitative Determination of HDL Cholesterol

By the same operation as in the measuring method of Example 5 except that the kit of Example 52 was used instead of the kit of Example 1, concentration of HDL cholesterol in each of 40 human serum samples was measured on Hitachi 7170 autoanalyzer.

COMPARATIVE EXAMPLE 28

Quantitative Determination of HDL Cholesterol

By the same operation as in the measuring method of Example 5 except that the kit of Comparative Example 25 was used instead of the kit of Example 1, concentration of HDL cholesterol in each of 40 human serum samples was measured on Hitachi 7170 autoanalyzer.

COMPARATIVE EXAMPLE 29

Quantitative Determination of HDL Cholesterol

By the same operation as in the measuring method of Example 5 except that the kit of Comparative Example 26 was used instead of the kit of Example 1, concentration of HDL cholesterol in each of 40 human serum samples was measured on Hitachi 7170 autoanalyzer.

COMPARATIVE EXAMPLE 30

Quantitative Determination of HDL Cholesterol

By the same operation as in the measuring method of Example 5 except that the kit of Comparative Example 27 was used instead of the kit of Example 1, concentration of HDL cholesterol in each of 40 human serum samples was measured on Hitachi 7170 autoanalyzer.

Correlation coefficients between a DCM and the measuring methods of Examples 53 to 58 or Comparative Examples 28 to 30 are shown in Table 5.

TABLE 5

| Method | Kit | | Correlation Coefficient |
|---|---|---|---|
| | First Reagent | Second Reagent | |
| Example 53 | Reagent V | Reagent h | 0.974 |
| Example 54 | Reagent W | Reagent i | 0.981 |
| Example 55 | Reagent W | Reagent h | 0.985 |
| Example 56 | Reagent X | Reagent h | 0.981 |
| Example 57 | Reagent Y | Reagent h | 0.990 |
| Example 58 | Reagent Z | Reagent h | 0.998 |
| Comp. Ex. 28 | Reagent V | Reagent b | 0.201 |
| Comp. Ex. 29 | Reagent W | Reagent b | 0.875 |
| Comp. Ex. 30 | Reagent U | Reagent h | 0.852 |

From the comparison between Examples 53 to 55 and Comparative Examples 28 to 30, it is proved that the measurement using kits comprising both of an anionic polyoxyethylene polycyclic phenyl sulfate and polyoxyethylene alkylamine correlates better to the measurement by a DCM than the measurement using kits comprising only one of polyoxyethylene polycyclic phenyl sulfate and polyoxyethylene alkylamine. Furthermore, from the comparison between Example 55 and Examples 56 to 58, it is also proved that a good correlation to the measurement by a DCM is observed in the measurement using kits comprising dextran sulfate and/or albumin in addition to enzymes for the measurement of cholesterol, polyoxyethylene polycyclic phenyl sulfate and polyoxyethylene alkylamine.

EXAMPLE 59

Quantitative Determination of HDL Cholesterol in Serum Originated from Patients Suffering from M Proteinemia By the operation similar to the measuring method of Example 5 using serums originated from patients suffering from M proteinemia as a sample and the kit of Example 1 as a kit, concentration of HDL cholesterol in each of serum samples was measured on Hitachi 7170 autoanalyzer. For each serum sample, absorbance 5 minutes after addition of the first reagent to each sample, i.e. absorbance (E1) of the reaction solution just before addition of the second reagent is shown in Table 6, and the measured value of HDL cholesterol for each serum sample is shown in Table 7. For comparison, the measured value obtained in the measurement of each of the serums originated from patients suffering from M proteinemia by a DCM is given in Table 7 as well.

COMPARATIVE EXAMPLE 31

Quantitative Determination of HDL Cholesterol in Serum Derived from Patients Suffering from M Proteinemia By the operation similar to the measuring method of Example 5 using serums originated from patients suffering from M proteinemia as a sample and the kit of Comparative Example 5 as a kit, concentration of HDL cholesterol in each of serum samples was measured on Hitachi 7170 autoanalyzer. For each serum sample, absorbance 5 minutes after addition of the first reagent to each sample, i.e. absorbance (E1) of the reaction solution just before addition of the second reagent is shown in Table 6, and the measured value of HDL cholesterol for each serum sample is shown in Table 7.

TABLE 6

| | Absorbance (E1) before Addition of Second Reagent (mAbs) | |
|---|---|---|
| Sample | Example 59 | Comparative Example 31 |
| M Proteinemia Sample 1 | 15.7 | 236.4 |
| M Proteinemia Sample 2 | 12.2 | 189.5 |
| M Proteinemia Sample 3 | 9.8 | 105.2 |
| Normal Sample | 6.2 | 6.1 |

As shown in Table 6, it is proved that turbidity caused by water-insoluble protein does not disappear in the measurement using the kit of Comparative Example 5 even before addition of the second reagent while turbidity caused by water-insoluble protein disappears before addition of the second reagent in the measurement using the kit of Example 1 comprising dextran sulfate.

TABLE 7

| | Measured Value (mg/dL) | | |
|---|---|---|---|
| Sample | Example 59 | Comparative Example. 31 | DCM |
| M Proteinemia Sample 1 | 28.2 | 47.3 | 31.2 |
| M Proteinemia Sample 2 | 15.5 | 9.5 | 16.0 |
| M Proteinemia Sample 3 | 22.8 | 26.1 | 22.8 |
| Normal Sample | 66.2 | 57.6 | 68.8 |

As shown in Table 7, the measured values obtained by the measurement (Example 59) using a kit of Example 1 were nearly the same as the measured values obtained by a DCM, but the measured values obtained by the measurement (Comparative Example 31) using a kit of Comparative Example 5 were greatly different from the measured values obtained by Example 59 or obtained by a DCM and did not reflect an accurate measurement. Accordingly, it is also proved that the kit of the present invention enables an accurate quantitative determination of HDL cholesterol even in samples originated from patients suffering from M proteinemia.

INDUSTRIAL APPLICABILITY

In accordance with the present invention, simple and accurate method for quantitative determination HDL cholesterol in a sample as well as a reagent and a kit used therefore are provided.

The invention claimed is:

1. A method for quantitatively determining cholesterol in high-density lipoprotein in a sample, which comprises:
   reacting the sample in an aqueous medium comprising a nonionic surfactant, polyanion and albumin with i) cholesterol esterase and cholesterol oxidase to form hydrogen peroxide or ii) cholesterol esterase, an oxidized coenzyme and cholesterol dehydrogenase to form a reduced coenzyme, wherein the nonionic surfactant is polyoxyethylene dodecylamine or polyoxyethylene octadecylamine, and the polyanion is dextran sulfate or a salt thereof;
   measuring formed hydrogen peroxide, or formed reduced coenzyme;
   correlating a measured value of hydrogen peroxide or a measured value of reduced coenzyme with an amount of cholesterol in high density lipoprotein by using a calibration curve; and
   determining a concentration of cholesterol in high-density lipoprotein in the sample.

2. The method according to claim 1, wherein the aqueous medium further comprises a bile acid derivative.

3. The method according to claim 2, wherein the bile acid derivative is present at 0.0001 to 10% of said aqueous medium.

4. The method according to claim 3, wherein the bile acid derivative is an anionic bile acid derivative.

5. The method according to claim 4, wherein said anionic bile acid derivative is selected from the group consisting of cholic acid, taurocholic acid, glycocholic acid, lithocholic acid, deoxycholic acid, chenodeoxycholic acid, ursodeoxycholic acid, 7-oxolithocholic acid, 12-oxolithocholic acid, 12-oxochenodeoxycholic acid, 7-oxodeoxycholic acid, hyocholic acid, hyodeoxycholic acid and dehydrocholic acid, or salts thereof.

6. The method according to any one of claims 1-4, 3 or 5, wherein said sample is reacted with 0.01 to 200 U/mL cholesterol esterase and 0.01 to 200 U/mL cholesterol oxidase.

7. The method according to any one of claims 1-4, 3 or 5, wherein said sample is reacted with 0.01 to 200 U/mL cholesterol esterase, oxidized coenzyme and 0.01 to 200 U/mL cholesterol dehydrogenase.

8. The method according to claim 1, wherein said sample is from a patient suffering from M proteinemia.

* * * * *

UNITED STATES PATENT AND TRADEMARK OFFICE
CERTIFICATE OF CORRECTION

| | | |
|---|---|---|
| PATENT NO. | : 7,851,174 B2 | |
| APPLICATION NO. | : 10/531315 | |
| DATED | : December 14, 2010 | |
| INVENTOR(S) | : Yuki Katayama et al. | |

It is certified that error appears in the above-identified patent and that said Letters Patent is hereby corrected as shown below:

ON COVER PAGE AT (54) TITLE:

"LIPOPROTEINS" should read --LIPOPROTEIN--.

COLUMN 1

Line 3, "LIPOPROTEINS" should read --LIPOPROTEIN--; and
Line 42, "methods" should read --method--.

COLUMN 3

Line 6, "avid" should read --avoid--.

COLUMN 8

Line 35, "poloxyethylene" should read --polyoxyethylene--; and "the" should read --and--.

COLUMN 10

Line 8, "a" should read --an--.

COLUMN 12

Line 43, "1)" should read --(1)--.

COLUMN 13

Line 58, "4-aminoantipyrine 4-AA)," should read --4-aminoantipyrine (4-AA),--.

Signed and Sealed this
First Day of March, 2011

David J. Kappos
*Director of the United States Patent and Trademark Office*

COLUMN 15

Line 16, "anonionicsurfactant," should read --a nonionic surfactant,--.

COLUMN 16

Line 5, "cholesterol accord-" should be deleted; and
Line 6, "ing to the present invention," should be deleted.

COLUMN 22

Line 36, "is preferred" (second occurrence) should be deleted;
Line 39, "never" should read --are not--; and
Line 64, "[polhyoxyethylene" should read --[polyoxyethylene--.

COLUMN 36

Line 20, "sample s" should read --samples--.

COLUMN 37

Line 19, "Examples 30," should read --Example 30,--.

COLUMN 40

Line 23,

" 
| HEPES (Ph 7.5) | 10 mmol/L |
|---|---|
| EMSE | 0.3 g/L |

" should read

--
| HEPES (Ph 7.5) | 10 mmol/L |
|---|---|
| EMSE | 0.3 g/L |
| Sodium dextran sulfate (molecular weight 500,000) | 1.0 g/L |
| Nymeen S207 | 0.07 g/L |

--; and

Lines 27-29, "Sodium dextran sulfate (molecular weight: 500,000) 1.0 g/L
Nymeen S207 0.07 g/L" should be deleted.

COLUMN 45

Table 4, "EXAMPLE 19" should read --Comp. Ex. 19--;
"EXAMPLE 20" should read --Comp. Ex. 20--;
"EXAMPLE 21" should read --Comp. Ex. 21--;
"EXAMPLE 22" should read --Comp. Ex. 22--;
"EXAMPLE 23" should read --Comp. Ex. 23--; and
"EXAMPLE 24" should read --Comp. Ex. 24--.

COLUMN 53

Line 6, "claims 1-4, 3 or 5," should read --claims 1-5,--.

COLUMN 54

Line 1, "claims 1-4, 3 or 5," should read --claims 1-5,--.